United States Patent
Saffell

(10) Patent No.: US 7,304,129 B2
(45) Date of Patent: Dec. 4, 2007

(54) PEPTIDES THAT STIMULATE CELL SURVIVAL AND AXON REGENERATION

(75) Inventor: Jane Louise Saffell, London (GB)

(73) Assignees: Imperial Innovations Limited, London (GB); King's College Innovations, London (GB)

(*) Notice: Subject to any disclaimer, the term of this patent is extended or adjusted under 35 U.S.C. 154(b) by 191 days.

(21) Appl. No.: 10/311,509

(22) PCT Filed: Jun. 18, 2001

(86) PCT No.: PCT/GB01/02660

§ 371 (c)(1),
(2), (4) Date: Aug. 15, 2003

(87) PCT Pub. No.: WO01/96364

PCT Pub. Date: Dec. 20, 2001

(65) Prior Publication Data

US 2004/0102370 A1    May 27, 2004

(30) Foreign Application Priority Data

Jun. 16, 2000 (GB) ................. 0014870.0

(51) Int. Cl.
C07K 7/06 (2006.01)
C07K 7/08 (2006.01)
C07K 14/00 (2006.01)
C07K 5/10 (2006.01)
C12N 5/08 (2006.01)

(52) U.S. Cl. ............ 530/328; 435/375; 435/383; 435/384; 435/387; 530/300; 530/327; 530/330

(58) Field of Classification Search ............. 514/2; 530/300, 323, 327, 328, 330, 333; 435/69.1
See application file for complete search history.

(56) References Cited

U.S. PATENT DOCUMENTS

| 5,108,898 | A | 4/1992 | Peters et al. |
| 5,792,743 | A | 8/1998 | Schachner |
| 5,837,813 | A | 11/1998 | Ruoslahti et al. |
| 5,840,689 | A | 11/1998 | Daniloff |
| 6,146,868 | A * | 11/2000 | Kozel et al. ............ 435/197 |
| 6,313,265 | B1 | 11/2001 | Phillips et al. |

FOREIGN PATENT DOCUMENTS

| WO | WO 8403087 A * | 8/1984 |
| WO | 00/72868 | 12/2000 |
| WO | WO 200148245 A2 * | 7/2001 |

OTHER PUBLICATIONS

Frei et al, 1992, Different extracellular comains of the neural cell adhesion molecule (N-CAM) are involved in different functions, Journal of Cell Biology, 118(1): 177-194.*
Dhople et al 2004, Conformation and activity of (-lysin and its analogs. Peptides, Article in Press, pp. 1-9.*
Neiiendam et al 2004, An NCAM-derived FGF-receptor agonist, the FGL-peptide, induces neurite outgrowth and neuronal survival in primary rat neurons. Journal of Neurochemistry, 91 : 920-935.*
Guerrini et al 2000. Structure-activity relationships of nociceptin and related peptides: comparison with dynorphin A. Peptides, 21: 923-933.*
LaVaille et al, 1995. Gene fusion expression systems in *Escherichia coli*. Current Opinion in Biotechnology, 6:501-506.*
Gozes, 2001. Neuroprotective peptide drug delivery and development: potential new therapeutics. Trends in Neuroscience, 24 (12): 700-705).*
Barthels et al, 1987. Isolation and nucleotide sequence of mouse NCAM cDNA that codes for a Mr 79,000 polypeptide without a membrane-spanning region. EMBO J, 6(10):3202.*
Lauta, 2000. Fundam Clin Pharmacol. 14(5): 425-442.*
Pettit et al. 1998. Trends Biotechnol. 16: 343-349.*
Todaro et al. 2004. Neurobiology of Disease. 15: 387-393.*
Ronn et al., "Neurite Outgrowth Induced by a Synthetic Peptide Ligand of Neural Cell Adhesion Molecule Requires Fibroblast Growth Factor Receptor Activation," *J. Neurochem.*, 75(2):665-71, 2000; Abstract only.
Stallcup, "The Third Fibronectin Type III Repeat is Required for L1 to Serve as an Optimal Substratum for Neurite Extension," *J. Neurosci. Res.*, 61:33-43, 2000.
Terada et al., "Improvement of Mammalian Cell Survival by Apoptosis-Inhibiting Genes and Caspase Inhibitors for Effective Use of Mammalian Cells," *Seibutsu Kogaku Kaishi*, 77(1):2-11, 1999; published as *Chemical Abstracts*, 130:310730, 1999.
Terada et al., "Improvement of Cell Survival by Inhibition of Caspases Playing Key Roles in Apoptosis," Abstract for meeting held 1997, published as *Proc. Annu. Meet. Jpn. Assoc. Anim. Cell Technol. 10th* (1999) and as *Chemical Abstracts*, 131:113335, 1999.
Derwents Patent Publication Abstract for Japanese Patent Application JP 04 198194; Jul. 17, 1992.
Doherty, P. and F. Walsh, "Cam-FGF Receptor Interactions: A Model for Axonal Growth." Molecular and Cellular Neuroscience, vol. 8, 1996, pp. 99-111.
Frei, T. et al., "Different Extracellular Domains of the Neural Cell Adhesion Molecule (N-CAM) Are Involved in Different Functions." The Journal of Cell Biology, vol. 118, No. 1, Jul. 1992, pp. 177-194.
European Search Report, EP 01940735.2 dated Jan. 31, 2007.

* cited by examiner

Primary Examiner—Elizabeth C. Kemmerer
Assistant Examiner—Zachary C. Howard
(74) Attorney, Agent, or Firm—Haynes and Boone LLP; Mark D. Moore

(57) ABSTRACT

Peptides which consist of or comprise the tetrameric peptide structural unit: Xaa-Xaa-Xaa-Xaa in which Xaa at position 1 represents Glu or Asp, Xaa at position 2 represents any amino acid, Xaa at position 3 represents any amino acid and Xaa at position 4 represents Glu or Asp, each of the meanings of Xaa being independent, and peptides which consist of or comprise the sequence PYSSTA, particularly when in multimeric form, mimic the beneficial trophic and neuritogenic effects of FGF but lack the undesirable mitogenic effects. They are useful for the treatment of conditions for which FGF has been proposed, including treatment of neurodegenerative diseases, ischaemia, wound healing and stimulation of angiogenesis in cardiac muscle.

14 Claims, 16 Drawing Sheets

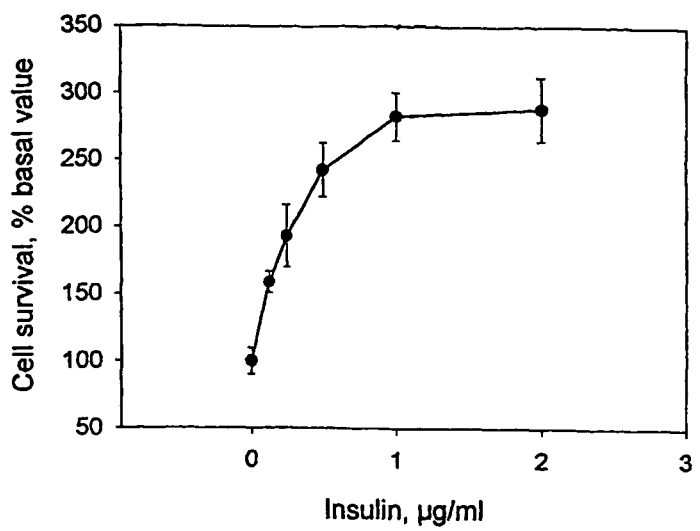
Figure 2a.i
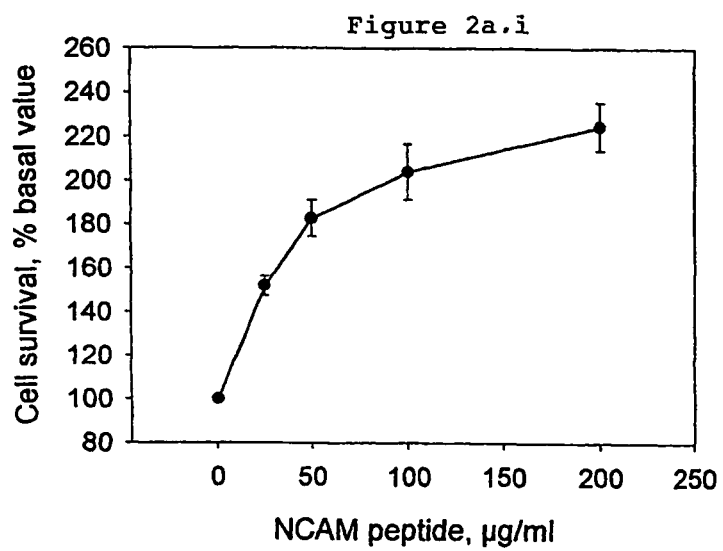
Figure 2a,ii
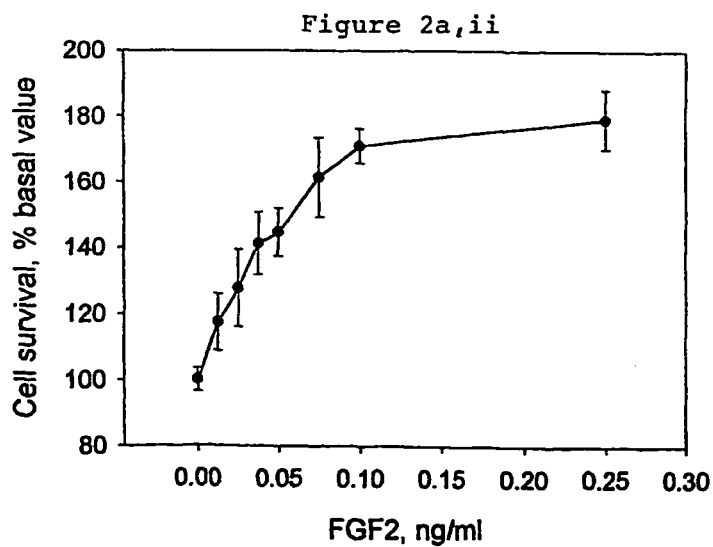
Figure 2a,iii

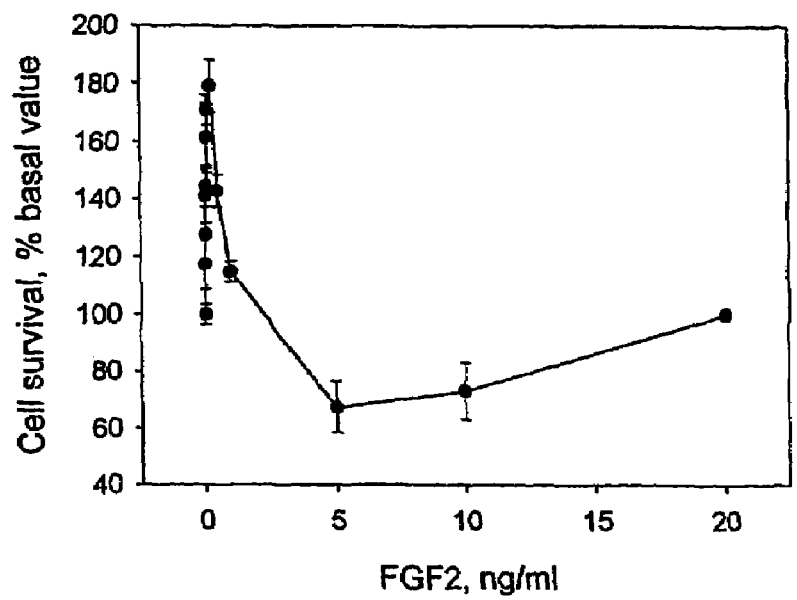
Figure 2e,i
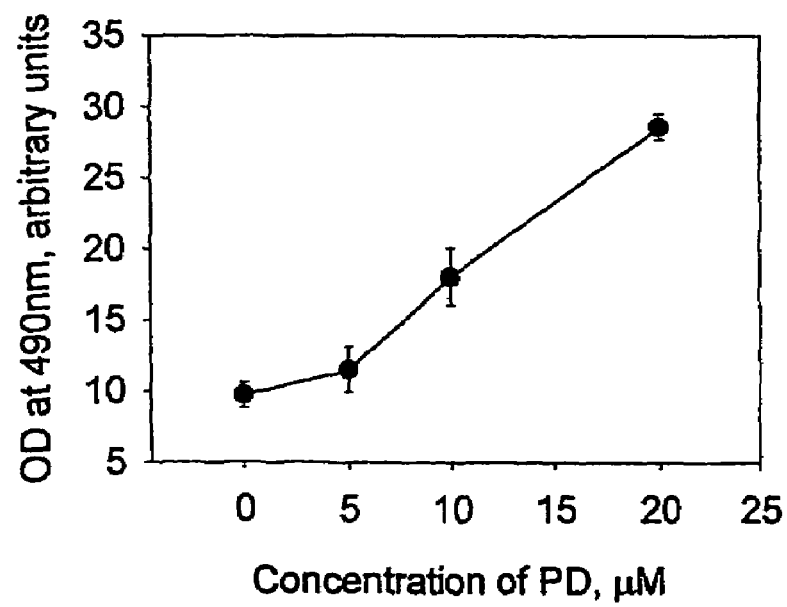
Figure 2e,ii

PEPTIDES THAT STIMULATE CELL SURVIVAL AND AXON REGENERATION

The present application is a nationalization of International Patent Application PCT/GB012660, filed Jun. 18, 2001, which claims priority to British priority application 0014870.0, filed Jun. 16, 2000.

FIELD OF THE INVENTION

This invention relates to neurodegenerative disease and nerve damage, and more particularly to stimulators of axonal regeneration and survival. The invention also relates to wound healing and angiogenesis.

The need to stimulate neurite outgrowth, which is also called axon regeneration, arises in the treatment of many diseases, including peripheral neuropathies (for example, diabetic or chemotherapy-induced), paralysis caused by spinal cord injury, motor neurone, disease, neurodegenerative diseases, for example, multiple sclerosis, Alzheimer's disease, and Parkinson's disease, and ischaemia, caused for example by stroke.

Many agents can stimulate neurite outgrowth in vitro. Growth factors, for example, nerve growth factor (NGF), fibroblast growth factor (FGF), glial cell derived growth factor (GDNF), brain derived growth factor (BDNF), and ciliary neurotrophic factor (CNTF) have trophic (cell survival-promoting) and axon regeneration effects, and there is much hope that they may be useful in the treatment of damaged or diseased nervous system. Some of the trophic factors have also been proposed for use in promoting wound healing. Many of the factors have been, are, or will be in clinical trial.

So far, however, the clinical improvements obtained with the above-mentioned materials have been very disappointing, mostly because of unwanted side-effects and short half life of the proteins in blood. Many of the growth factors mentioned above are mitogenic, and entail the risk that they can stimulate tumour formation.

SUMMARY OF THE INVENTION

The present invention is based on the development of synthetic peptides, of much smaller molecular size than the prior materials, whose in vitro performance in stimulating axon regeneration and cell survival is comparable to that of the growth factors mentioned above. The novel peptides are (a) less prone to proteolysis and therefore should have a long half life in blood, (b) cheap and easy to produce in quantity, and (c) stable and easy to store without changes in activity between batches. These peptides do not stimulate mitogenesis and are therefore safer in this respect.

The peptides of the present invention appear inter alia, to mimic the beneficial trophic and neuritogenic effects of fibroblast growth factor (FGF) of high affinity receptor activation but to lack the undesirable mitogenic and apoptotic effects of FGF. The peptides of the invention may therefore be used in any of the situations where FGF is used, for example, they may be used for the treatment of any of the pathological conditions for which FGF has been proposed. Such conditions include conditions requiring stimulation of neurite outgrowth, conditions requiring stimulation of cell survival, for example, in neurodegenerative diseases, peripheral neurophathies, paralysis caused by spinal cord injuries, nerve damage caused by surgery or trauma, and ischaemia, for example caused by stroke, and in the treatment of multiple sclerosis (MS). The peptides may also be used to promote wound healing and to stimulate angiogenesis in cardiac muscle.

A further aspect of the invention relates to the inhibition of undesirable effects of FGF, for example, angiogenesis into tumours.

Accordingly, the present invention provides a pharmaceutical composition comprising a peptide of the invention in admixture with a pharmaceutically suitable carrier.

The invention also provides methods of treatment of a disease, disorder or pathological condition in a mammalian subject, especially a human subject, comprising administering to a subject in need of such treatment an amount of a peptide of the invention effective for said treatment. The disease, disorder or pathological condition is especially as mentioned above, and in more detail below.

The invention also provides a peptide of the invention for use as a medicament, for example, in the treatment of a disease, disorder or pathological condition as described above and below, and further provides the use of a peptide of the invention for the manufacture of a medicament for the treatment of a disease, disorder or pathological condition as described above and below.

The peptides of the invention may be prepared by chemical synthesis or recombinantly. As an alternative to the use of a peptide of the invention, a nucleic acid molecule encoding a peptide of the invention may be used in gene therapy, either in vivo or ex vivo.

BRIEF DESCRIPTION OF THE FIGURES

FIGS. 1a to 1h show the effect of various peptides of the invention on neurite outgrowth. FIGS. 1a to 1d compare the effect of peptides with soluble NCAM (Neuronal Cell Adhesion Molecule). The peptides used in FIGS. 1a to 1k are the following:

FIG. 1a: the 13-mer Ac-SIDRVEPYSSTAQ-amide.
FIG. 1b: the 10-mer Ac-DRVEPYSSTA-amide.
FIG. 1c: the tetramer Ac-DRVE-amide.
FIG. 1d: the 6-mer Ac-PYSSTA-amide.
FIG. 1e: the 10-mers Ac-DRVEPYSSTA-amide, Ac-ARVEPYSSTA-amide, Ac-DRSEPYSSTA-amide, Ac-ARSEPYSSTA-amide.
FIG. 1f: Peptide A(d), the multimeric peptide [{Ac-DRVEPYSSTA}$_2$-K]$_2$-K-OH.
FIG. 1g: the peptide Ac-DRVE-amide
FIG. 1h: the peptide Ac-EGME-amide
FIG. 1i shows the effect of FGF2 on cerebellar neurite outgrowth.
FIG. 1j shows that 25 µl of peptide Ac-DRVEPYSSTA-amide inhibits neurite outgrowth stimulated by FGF2.
FIG. 1k shows that cerebellar neurons from transgenic mice expressing dominant negative FGF receptors in neurons are not able to extend neurites in response to the peptide Ac-DRVEPYSSTA-amide.

FIGS. 2a to 2i show the results of cell survival assays.
FIG. 2a shows the effects of insulin. (FIG. 2a,i), Peptide A(d) (FIG. 2a,ii) and FGF2 (FIG. 2a,iii) on the survival of T3T cells in serum-free medium.
FIG. 2b shows the effects of the multimeric peptide Ac-DRVEPYSSTA[lys]$_2$[lys], i.e. peptide A(d), the "scrambled" multimeric peptide Ac-ADTRSVSEYP[lys]$_2$[lys], and the "mutated" multimeric peptide Ac-ARSEPYSSTA [lys]$_2$[lys].
FIG. 2c shows the effects of the peptides Ac-DRVE-amide and Ac-EGME-amide.

FIG. 2d shows the effects of FGF2 and Peptide A(d) on the survival of L6 cells, which lack FGF2 receptors. FIG. 2d compares-the effects of DMEM, FCS, FGF2 at 0.1, 1 and 10 ng/ml, insulin at 0.5 and 5 μg/ml, and Peptide A(d) at 100 and 400 μg/ml.

FIG. 2e,i shows the effect of FGF2 on 3T3 cell survival, demonstrating stimulation of cell survival at low concentrations and stimulation of apoptosis at high concentrations.

FIG. 2e,ii shows the effects of inhibiting MAP kinase on cell survival in the presence of 10 ng/ml FGF2. The figure shows that the apoptotic effect of FGF2 can be reversed by supplementation with an inhibitor of MAP kinase signalling.

FIG. 2f is a Western blot showing that FCS, 1 and 10 ng/ml FGF2 stimulate MAP kinase activation, while 0.1 ng/ml FGF2, the peptide Ac-DRVEPYSSTA[lys]2[lys], and insulin do not.

FIG. 2g shows the effects of NGF, FGF2 and Peptide A(d) on survival of neurons.

FIG. 2h shows the effects of that Peptide A(d) on survival of oligodendrocytes in vitro.

FIG. 2i shows cells cultured for three days in the presence of DMEM alone, or supplemented with insulin, FGF2 or Peptide A(d). Cells do not survive in the DMEM alone. Supplementation with insulin, low concentrations of FGF2 or Peptide A(d) stimulate cell survival.

DETAILED DESCRIPTION OF THE INVENTION

Figure 1A:
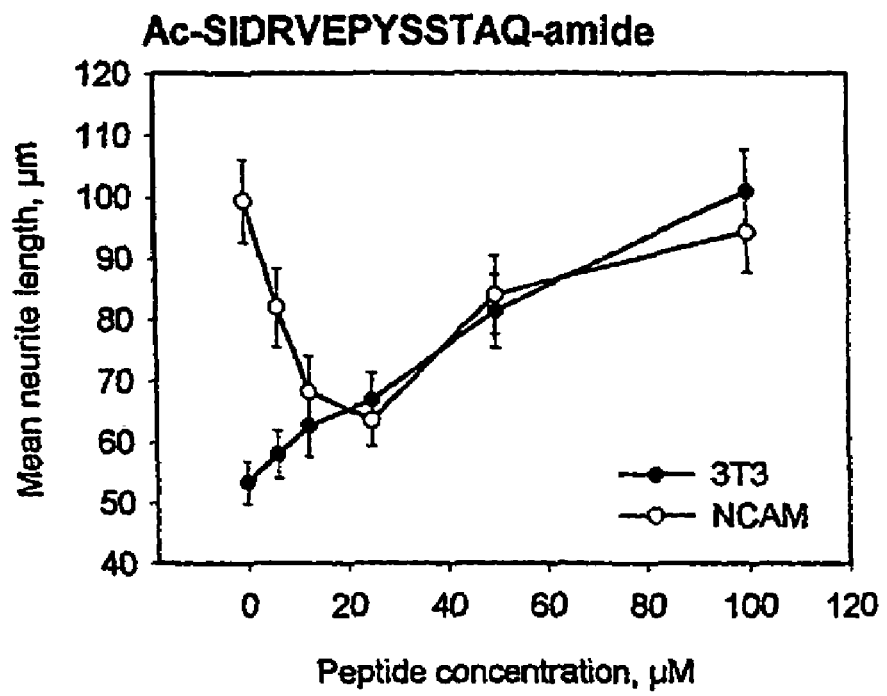
FIGS. 1a to 1k show the results of neurite outgrowth assays.

The present invention provides peptides which consist of or comprise the essential tetrameric peptide structural unit:

Xaa-Xaa-Xaa-Xaa                    [SEQ.ID.NO.:1]

in which Xaa at position 1 represents Glu or Asp, Xaa at position 2 represents any amino acid, Xaa at position 3 represents any amino acid and Xaa at position 4 represents Glu or Asp. Each of the meanings of Xaa is independent, that is to say, the residues at positions 1 and 4 may be the same as each other or may be different, and the residues at positions 2 and 3 may be the same as each other or different, and each may be the same as a residue at positions 1 and 4 or may be different.

A peptide of the present invention may have an acyl group as substituent at the N-terminus and/or may be amidated at the carboxy terminus, for example, with an unsubstituted or substituted amine group. An amino group may have one, two or three substituents, which may be the same or different, for example, selected from lower alkyl groups, in particular alkyl groups having up to four carbon atoms. An acyl group is preferably a lower acyl group, for example, having up to four carbon atoms, especially an acetyl group.

A peptide of the invention may comprise the tetrameric structural unit set out above as part of a longer (extended) peptide molecule, some examples of which are given below. A peptide of the present invention, in the form of a tetrameric structural unit as defined above or in the form of a longer peptide comprising such a unit may be present in a multimeric form, for example, as described below. The term "multimeric" includes "dimeric". One or more peptides may be linked to a backbone structure, also called a scaffold molecule.

A peptide of the invention that comprises two cysteine residues may be cyclised by formation of a disulphide bond between the two cysteine residues.

The tetrameric peptide structural unit may be any one of the following:

| Glu-Xaa-Xaa-Glu | [SEQ.ID.NO.:2] |
| Glu-Xaa-Xaa-Asp | [SEQ.ID.NO.:3] |
| Asp-Xaa-Xaa-Glu | [SEQ.ID.NO.:4] |
| Asp-Xaa-Xaa-Asp | [SEQ.ID.NO.:5] | in which each residue Xaa independently represents any amino acid.

In the tetrameric peptide structural unit the amino acids at positions 2 and 3 may be natural or unnatural amino acids, for example they may be L-amino acids or D-amino acids, but are preferably L-amino acids. Modified amino acids, for example, 4-hydroxyproline, gamma-carboxyglutamic acid, o-phosphoserine, o-phosphotyrosine and delta-hydroxylysine may be used.

It may be preferable to select the amino acids for positions 2 and 3 from arginine (R), glycine (G), methionine (M) and serine (S).

Examples of preferred tetrameric structural units are the following: DRVE [SEQ.ID.NO.:6], EGME [SEQ.ID.NO.:7], EMGE [SEQ.ID.NO.:8], DRSE [SEQ.ID.NO.:9], DAVE [SEQ.ID.NO.:10], EVRD [SEQ.ID.NO.:11], EGGE [SEQ.ID.NO.:12].

As indicated above, a tetrameric peptide structural unit may be part of a longer peptide. Such a peptide of the invention may comprise, for example, up to 30 amino acids residues, for example, up to 25 amino acids residues, for example, up to 20 amino acids residues, for example, up to 15 amino acids residues, for example, 15, 14, 13, 12, 11, 10, 9, 8, 7, 6, or 5 amino acids residues.

A peptide of the present invention may comprise the tetrameric structural unit and the sequence PYSSTA [SEQ.ID.NO.: 13] or part of that sequence, preferably at the C-terminus of the tetrameric unit.

Examples of longer peptides of the present invention are the following: DRVEPYSSTA, EGMEGM, DRSEPYSSTA, DAVEPYSSTA. A peptide of SEQ.ID.NO.:14, 15, 16 or 17 may be extended at the N-terminus, at the C-terminus or at both termini. The N-terminus may be extended, for example, by an isoleucine residue (I) or by serine-isoleucine (SI), and the C-terminus may be extended by a glutamine residue (Q). An example of such an extended peptide is SIDRVEPYSSTAQ.

Certain of the sequences set out above, in particular sequences consisting of or comprising the tetrameric structural unit DRVE [SEQ.ID.NO.:6] are derived from the first fibronectin type III repeat of NCAM, the neuronal cell adhesion molecule. The inventor has found that a soluble NCAM-Fc chimeric molecule containing the first fibronectin type III domain (FNIII) stimulates survival of NIH T3T cells, whereas a soluble NCAM chimeric molecule lacking the first and second FNIII domains is unable to stimulate survival of NIH T3T cells. The NCAM molecule may have the sequence from any suitable species. Preferably the sequence is that of a human NCAM molecule, including any human isoform of NCAM. The first fibronectin type III repeat of NCAM extends from proline at position 510 to glysine at position 600 of the human 140 kd isoform (SEQ.ID.No. 21) (see databank entry GI:3334473), and the peptide of the invention may have any corresponding sequence of any other isoform or any other NCAM molecule.

Accordingly, the present invention provides a peptide that consists of or comprises the first fibronectin type III repeat of NCAM or any subsequence thereof, in particular any subsequence that comprises the tetrameric structural unit DRVE [SEQ.ID.NO.:6]. The peptide of the invention may be:

1) A peptide consisting of or comprising the first fibronectin type III repeat of NCAM;
2) A peptide consisting essentially of the first fibronectin type III repeat of NCAM or a peptide consisting essentially of or comprising a part of the first fibronectin type III repeat of NCAM.
3) A peptide of 1) or 2) with other sequences from NCAM, for example one or more other NCAM domains.
4) A peptide of any one of 1), 2) or 3) as part of a fusion protein with non-NCAM sequences, e.g. an NCAM-Fc fusion peptide.

The peptide may be an NCAM molecule lacking one or more domains providing that the first fibronectin type III repeat domain is present. The invention does not include the complete NCAM molecule or the use thereof.

The peptide of the invention may be a sequence having homology with one of sequences 1) to 4) above with the beneficial trophic and neuritogenic effects of FGF but lacking the undesirable mitogenic effects of FGF, which beneficial properties are displayed by other peptides of the invention, for example of sequence ID.No.1. The homology may be at the amino acid level or at the nucleic acid level. At the amino acid level, the sequence may have substitutions, additions or deletions. Substitutions are preferably conservative substitutions. The homology is preferably at least 80%, especially at least 90%, for example at least 95% at the amino acid level with a corresponding NCAM sequence, for example the 140 kD isoform (SEQ.ID.No 21).

The peptide PYSSTA [SEQ.ID.NO.: 13] is also a subsequence of the first fibronectin type III repeat of NCAM. Accordingly, peptide PYSSTA, any peptide consisting of three or more, especially four or five contiguous amino acids of peptide PYSSTA, and any peptide that comprises peptide PYSSTA or three or more, especially four or five contiguous amino acids of that peptide, is also part of the invention. In the sequence PYSSTA, there may-be one or more substitutions, for example one or two substitutions, especially conservative substitutions provided that the beneficial trophic and neuritogenic effects of FGF and the lack of the undesirable mitogenic effects of FGF (which beneficial effects are exhibited by the PYSSTA parent sequence) are retained. Peptides that comprise the sequence DRVE and all or part of the sequence PYSTTA are particularly preferred.

Peptides tend to be more flexible than proteins because peptides lack the higher levels of organisation that tend to maintain conformation in proteins. Cyclic peptides often have an advantage over linear peptides in that their cyclic structure is more rigid and hence their biological activity may be higher than that of the corresponding linear peptide. Peptides of the present invention may be linear or may be cyclic. As described above, two or more cysteine residues may be provided in the peptide, thereby enabling formation of one or more disulphide bonds. The cysteine residues should not interrupt the tetrameric structural unit defined above, but may be at any other positions in the peptide molecule. It may be preferable to provide cysteine residues at or near the ends of the peptide molecule. For example, a cysteine residue may be provided at the N-terminus and at the C-terminus of any of the peptides set out above, for example, CDRVEPYSSTAC [SEQ.ID.NO.:18].

Any peptide of the present invention, whether a tetrameric structural unit as such or a longer peptide comprising such a structural unit may be acylated at the amino terminus and/or may be amidated at the carboxy terminus, as described above. Amino acid side chains may also be modified, for example, at positions 2 and 3 of the tetrameric structural unit.

Any peptide of the invention may be reversed, that is to say, the N-terminal residue becomes the C-terminal residue and the sequence is written backwards. For example, the sequence DRVE [SEQ.ID.NO.:6] when reversed is EVRD, The invention includes all peptides in reversed form.

Figure 5:
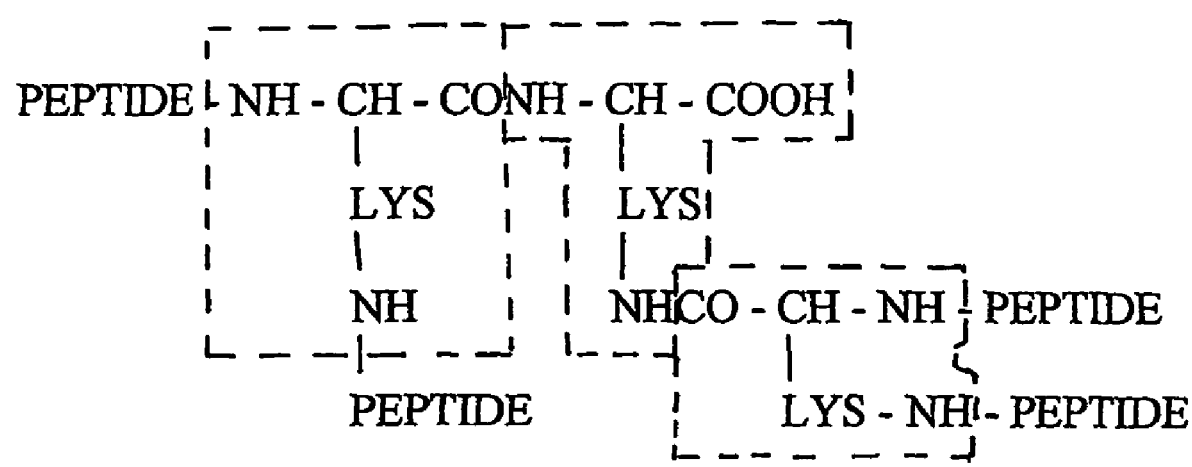
FIG. 5 shows a generic multimer, denrimeric peptide having four peptide units on a backbone structure of three lysine residues.

Any peptide of the present invention may be in multimeric form, that is to say, two or more peptides of the invention may be linked together via a backbone structure or scaffold molecule. Sometimes a smaller structure is called a linker group and a larger structure is called a backbone structure or scaffold molecule. However, the term "backbone structure" is used herein to denote the structure to which the peptides are linked, regardless of its size. The nature of the backbone structure is not critical, and many different different types of molecules may be used. One example of a backbone structure is an oligolysine molecule, for example, having two or more lysine residues, for example two, three or more lysines. Two or more peptides of the invention, for example, two three or four peptides may be attached to the lysine molecules, for example, to the amino side chains. A backbone structure, for example, an oligolysine molecule, may be linear or branched. A multimeric peptide of the invention on a branched backbone molecule may be referred to herein as a "dendrimeric" peptide. A generic, multimeric, dendrimeric peptide having four peptide units linked to a backbone structure of three lysine residues is shown in FIG. 5.

The following are examples of peptides of the invention.
1. Peptide A: Acetyl-DRVEPYSSTA-amide The peptide DRVEPYSSTA is SEQ.ID.NO.:14
2. The Multiple Antigenic Peptide A(d): [{Ac-DRVE-PYSSTA}$_2$-K]$_2$-K-OH where Ac represents an acyl group, for example a lower acyl group, for example, having from 1 to 4 carbon atoms. This peptide is also referred to herein as Ac-DRVEPYSSTA[lys]2[lys]and as DRVEPYSSTA[lys]2[lys].

3. Peptide B: Acetyl-DRVE-amide
  DRVE is SEQ.ID.NO.:6
4. Peptide C: Acetyl-EGME-amide EGME is SEQ.ID.NO.:7
5. Peptide D: Acetyl-EGMEGM-amide EGMEGM is SEQ.ID.NO.:15
6. Peptide E: Acetyl-DRSEPYSSTA-amide DRSEPYSSTA is SEQ.ID.NO.:16
7. Peptide F: Acetyl-DAVEPYSSTA-amide
  DAVEPYSSTA is SEQ.ID.NO.:17.

The invention also includes the reversed forms of the peptides of SEQ.ID.NOS.: 14, 6, 8, 15, 16 and 17, also of peptides A to E, for example, the reversed form of peptide SEQ.ID.NO.: 14 is ATSSYPEVRD. The reversed form of peptide A is Acetyl-ATSSYPEVRD-amide.

Figure 4:
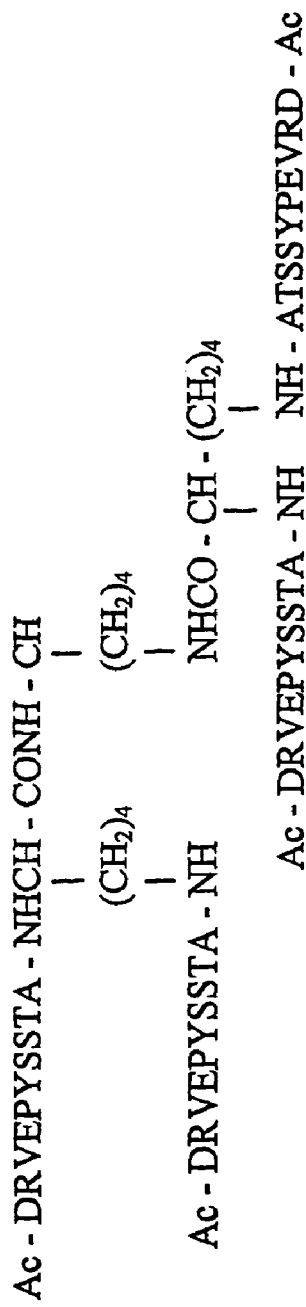
FIG. 4 shows the structure of the multimeric, dendrimeric Peptide A(d).
Figure 4:
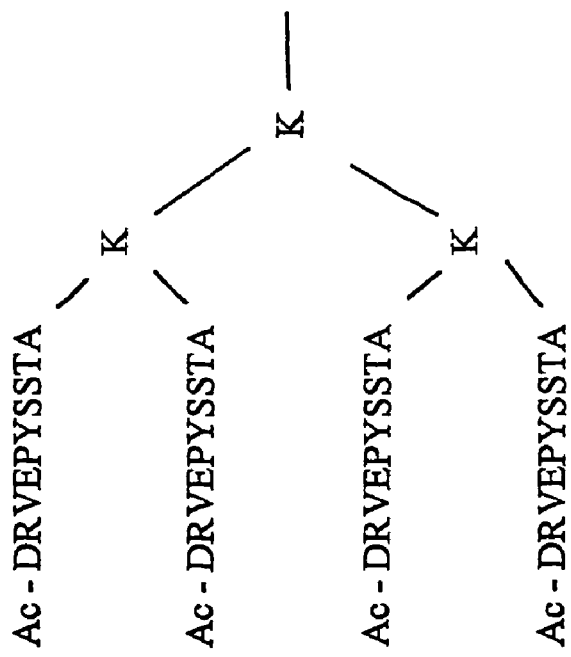

A peptide of the present invention, for example, one of the peptide molecules B to F above, or a reversed form of such a peptide, may form part of an extended structure by attachment to a suitable backbone structure, for example, as described above. For example, analogues of Peptide A(d) may be provided. Peptide A(d) has four units of peptide A (DRVEPYSSSTA) linked to a branched oligolysine backbone structure composed of three lysine residues, forming a "dendrimeric" peptide. FIGS. 4 and 5 show the structure of Peptide A(d).

Analogues of Peptide A(d) have four units of the respective acetylated peptide linked to the oligolysine backbone via one or more linker residues. For example, any of the following peptides may be linked to a branched backbone of three lysine residues: acetyl-DRVE-$(X)_n$-, acetyl-EGME-$(X)_n$-, acetyl-EMGE-$(X)_n$-, acetyl-DRSE-$(X)_n$-, acetyl-DAVE-$(X)_n$-, acetyl-EVRD-$(X)_n$-, acetyl-EGGE-$(X)_n$-, acetyl-EGMEGM-$(X)_n$-, acetyl-DRSEPYSSTA-$(X)_n$-or acetyl-DAVEPYSSTA-$(X)_n$-, in which X is a linker residue or s direct bond and n is an integer of one or more, for example, 1, 2 or 3. Suitable linkers are known and include, for example, the dimer GS (glycine-serine) and multiples thereof, for example, GSGS and GSGSGS. An anlogue may comprise a reversed form of a peptide.

Any of the other peptides of the present invention may be linked to a backbone structure to form a multimeric peptide. For example, a peptide that consists of or comprises the first fibronectin type III repeat of NCAM or any subsequence thereof, in particular any subsequence that comprises the tetrameric structural unit DRVE [SEQ.ID.NO.:6] or, for example, the peptide PYSSTA [SEQ.ID.NO.: 13] or any peptide that consists or comprises all or part of that sequence. Again, reversed sequences may be used.

The peptides of the present invention stimulate axon regeneration, neurite outgrowth, and cell survival, including survival of neurons, oligodendrocytes and fibroblasts. As pointed out above, they demonstrate effects comparable to those obtained using various growth factors, for example, nerve growth factor (NGF), fibroblast growth factor (FGF), glial cell derived growth factor (GDNF), brain derived growth factor (BDNF), and ciliary neurotrophic factor (CNTF), in particular FGF. As stated above, they appear to mimic the trophic and neuritogenic effects of FGF. These effects are observed at low concentrations of FGF. Moreover, the peptides of the invention have an advantage over such growth factors, including FGF, in that they do not appear to have the disadvantageous mitogenic and apoptotic properties that generally accompany the useful growth stimulating properties of the conventional growth factors. These effects are observed with FGF at high concentrations. The peptides appear to act by binding to and activating FGF receptors.

The need to stimulate neurite outgrowth arises in the treatment of many diseases, including peripheral neuropathies, for example, diabetic neuropathy or chemotherapy-induced neuropathy; paralysis caused by spinal cord injury; neurodegenerative diseases, for example, motor neurone disease, multiple sclerosis, Alzheimer's disease, Huntingdon's disease, Parkinson's disease, PSP (progressive supranuclear palsy) and prion diseases; and ischaemia, caused for example by stroke; to stimulate angiogenesis in cardiac muscle; and in restoration of nerve function after trauma or surgery.

The peptides of the present invention also stimulate cell survival. In this they seem to mimic the useful trophic and neuritogenic effects of FGF without having the undesirable mitogenic and apoptotic effects. This is a general effect on cell survival, which is observed for example, in neurons, in oligodendrocytes, and in fibroblasts. The ability of a peptide of the present invention to stimulate cell survival, in particular survival of neurons, enhances its effect on axon regeneration.

Oligodendrocytes are involved in the myelination of nerve cells. Demyelination is a key factor in multiple sclerosis (MS). The ability of the peptides of the present invention to stimulate the survival of oligodendrocytes makes them useful in the treatment of MS.

Fibroblasts are involved in wound healing, so the ability to stimulate fibroblast survival is important in promoting wound healing. Wounds include those caused, for example, by trauma, by surgery, by burns, for example, thermal burns, chemical burns and radiation burns, and also other radiation damage, for example, caused by radiotherapy.

The observations of the effects of the peptides of the present invention on cell growth and survival indicates that they appear inter alia, to mimic the beneficial trophic and neuritogenic effects of fibroblast growth factor (FGF) of high affinity receptor activation but to lack the undesirable mitogenic and apoptotic effects of FGF. The peptides of the invention may therefore be used in any of the situations where therapeutic use FGF has been proposed, or would be proposed were it not for the adverse side effects.

Accordingly, the present invention provides a method of stimulating neurite outgrowth in a mammalian subject, especially a human subject, comprising administering to a subject in need of such treatment an amount of a peptide of the invention effective for neurite outgrowth promotion.

The present invention also provides a method of stimulating cell survival in a mammalian subject, especially a human subject, comprising administering to a subject in need of such treatment an amount of a peptide of the invention effective for said cell survival promotion.

The method may be used, for example, for the stimulation of the survival of any cells whose survival is stimulated by FGF. For example, the method may be used to stimulate the survival of cells selected from neurones, oligodendrocytes and fibroblasts.

The present invention also provides a method of treatment of a neurodegenerative disease in a mammalian subject, especially a human subject, comprising administering to a subject in need of such treatment an amount of a peptide of the invention effective for said treatment.

A neurodegenerative disease is, for example, motor neurone disease, multiple sclerosis, Alzheimer's disease, Parkinson's disease, Huntingdon's disease, PSP (progressive supranuclear palsy) or a prion disease.

The present invention also provides a method of treatment of a peripheral neuropathy in a mammalian subject, especially a human subject, comprising administering to a subject in need of such treatment an amount of a peptide of the invention effective for said treatment.

A peripheral neuropathy is, for example, diabetic neuropathy or chemotherapy-induced neuropathy.

The present invention also provides a method of treatment for stimulating or restoring nerve function after trauma or surgery in a mammalian subject, especially a human subject, comprising administering to a subject in need of such treatment an amount of a peptide of the invention effective for said treatment.

The nerve function to be stimulated or restored may be local nerve function. This method of the invention may also be used in the treatment of paralysis caused by spinal cord injuries.

The present invention also provides a method of stimulating angiogenesis in cardiac muscle in a mammalian subject, especially a human subject, comprising administering to a subject in need of such treatment an amount of a peptide of the invention effective for said treatment.

The present invention also provides a method of treatment of ischaemia in a mammalian subject, especially a human subject, for example, ischaemia caused by a stroke, comprising administering to a subject in need of such treatment an amount of a peptide of the invention effective for said treatment.

In a further aspect, a peptide of the present invention may be used to inhibit an undesirable effect of FGF, for example, angiogenesis into tumours. Tumours require blood and secrete factors including FGF to stimulate the growth of blood vessels into themselves. A peptide of the present invention maybe able to block FGF binding to its receptor without itself stimulating the receptor, thus inhibiting the angiogenic effect of FGF.

The present invention thus provides a method of inhibiting or reducing angiogenesis in a tumour in a mammalian subject, especially a human subject, comprising administering to a subject in need of such treatment an amount of a peptide of the invention effective for said inhibition.

The present invention also provides a peptide of the invention for use as a medicament, especially for any of the methods of treatment described above.

The invention further provides the use of a peptide of the invention for the manufacture of a medicament, particularly for any of the methods of treatment described above.

A peptide of the invention should be administered by a route appropriate for the condition to be treated and for the treatment desired. Such routes include intradermal, intramuscular, intraperitoneal, intravenous, subcutaneous, intranasal, epidural, and oral routes. The peptides may be administered by any convenient route, for example by infusion or bolus injection, by absorption through epithelial or mucocutaneous linings for example, oral mucosa, rectal and intestinal mucosa, and may be administered together with other biologically active agents. Administration can be systemic or local.

The present invention provides a pharmaceutical composition comprising a therapeutically effective amount of peptide of the invention and a pharmaceutically suitable carrier. The term "carrier" includes diluents, adjuvants, excipients, and vehicles with which the peptide is administered. The term carrier also includes wetting and emulsifying agents, and pH buffering agents which, if present, are generally present in minor amounts. Compositions of the invention can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will contain a therapeutically effective amount of the peptide, preferably in purified form, together with a suitable amount of carrier so as to provide the form for proper administration to the patient. The formulation should suit the mode of administration. The journal "Advanced Drug Delivery Reviews" is a useful source of information on new and more sophisticated pharmaceutical formulations.

In one embodiment, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lignocaine to ease pain at the site of the injection. For administration to promote wound healing, it is preferable to provide a formulation suitable for topical application, for example, a cream or ointment. Impregnated dressings and sprays are particularly useful.

For treatment of neurodegenerative diseases that involve brain degeneration, it is preferable to use a formulation suitable for delivery of the peptide across the blood-brain barrier. Examples of suitable formulation are given in "Delivery of peptides, and proteins through the blood-brain barrier" Bickel U et al. Advanced Drug Delivery Reviews 46, 247-279.

The amount of the peptide of the invention which will be effective in the treatment of a particular disorder or condition will depend on the nature of the disorder or condition, and can be determined by standard clinical techniques. In addition, in vitro assays may optionally be employed to help identify optimal dosage ranges. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal test systems.

A peptide of the present invention may be produced by conventional methods of chemical synthesis, for example, using the Merrifield technique. Such methods are well known and well documented.

Alternatively, a peptide, particularly a longer peptide of the invention, may be produced recombinantly. A nucleic acid encoding the peptide may be synthesised chemically or the domain of the NCAM gene comprising the first fibronectin type III repeat may be used. The sequence of the human 140 kd isoform of NCAM is available under the database reference GI:3334473. The first fibronectin type III repeat in that sequence comprises the amino acids from proline at position 510 to glysine at position 600. B28 cells stably infected with wild-type human L1 NCAM cDNA have been described (Lin et al 1996 J Cell Biochem 63:463-477 & Lin et al 1996 Mol Biol Cell 7:1977-1993, Zisch et al, 1997 J Neurosci Res 47:695-665 & Dahlin-Huppe 1997 Mol Cell Neurosci 9:144-156).

For recombinant expression of a peptide of the invention the nucleic acid encoding the peptide can be inserted into an appropriate expression vector, i.e., a vector that contains the necessary elements for the transcription and translation of the inserted coding sequence. In a preferred embodiment, the regulatory elements for example, promotor, are heterologous i.e., not the native gene promotor. Promotors which may be used include the SV40 early promoter (Bernoist and Chambon, 1981, Nature 290: 304-310), and the promoter contained in the 3' long terminal repeat of Rous sarcoma virus (Yamamoto et al., 1980, Cell 22: 787-797), among others.

A variety of host vector systems may be utilized to express the peptide encoding sequence. These include mammalian cell systems infected with virus for example, vaccinia virus and adenovirus; insect cell systems infected with virus, for example, baculovirus; microorganisms for example yeast containing yeast vectors; or bacterial transformed with bacteriophage, DNA, plasmid DNA, or cosmid DNA.

When a peptide of the invention has been recombinantly expressed, it may be isolated and purified by standard methods including chromatography for example, ion exchange, affinity, and sizing column chromatography, centrifugation, differential solubility, or by any other standard technique for the purification of proteins and peptides.

As indicated above, an alternative to administration of a peptide of the invention is the administration of a nucleic acid molecule encoding the peptide, that is to say, using gene therapy.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3.:87-95; Tolstoshev, 1993, 30 Ann. Rev.

Pharmacol. Toxicol. 32:573-596; Mulligan, 1993, Science 260:926-932; and Morgan and Anderson, 1993, Ann. Rev.

Biochem. 62:191-217; May, 1993, TIBTECH 11(5):155-215.

Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid encoding a peptide of the invention for use in gene therapy is part of an expression vector that expresses peptide in a suitable host. In particular, such a nucleic acid has a promoter operably linked to the peptide coding region, said promoter being inducible or constitutive, homologous or heterologous and, optionally, tissue-specific. In another particular embodiment, a nucleic acid molecule is used in which peptide coding sequence and any other desired sequences are flanked by regions that promote homologous recombination at a desired site in the genome, thus providing for intrachromosomal expression of the peptide encoding nucleic acid, as described (Koller and Smithies, 1989, Proc. Natl. Acad. Sci. USA 86:8932-8935; Zijlstra et al., 1989, Nature 342: 435-438). In another embodiment, a nucleic acid encoding a peptide of the invention, preferably operably linked to a promoter, is delivered by gene therapy methods.

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92).

In such an embodiment of the invention in which recombinant cells are used in gene therapy, a nucleic acid encoding a peptide of the invention is introduced into the cells such that they are expressible by the cells or their progeny, for example, as described above, and the recombinant cells are then administered in vivo for therapeutic effect. In a specific embodiment, stem or progenitor cells are used. Any stem and/or progenitor cells which can be isolated and maintained in vitro can potentially be used, such as hematopoietic stem cells (HSC), stem cells of epithelial tissues such as the skin and the lining of the gut, embryonic heart muscle cells, liver stem cells (PCT Publication WO 94/08598, dated Apr. 28, 1994), neural stem cells (Stemple and Anderson, 1992, Cell 71:973-985), or epithelial stem cells (ESCs) (Rheinwald, 1980, Meth. Cell Bio-21A:229; Pittelkow and Scott, 1986, Mayo Clinic Proc. 61:771).

Various delivery systems are known and can be used to administer a nucleic acid that encodes a peptide of the invention, for example, encapsulation in liposomes (Langer, Science 249:1527-1533 (1990); Treat et al., in Liposomes in the Therapy of Infectious Disease and Cancer, Lopez-Berestein and Fidler (eds.), Liss, New York, pp. 353-365 (1989)), microparticles, microcapsules, recombinant cells capable of expressing the nucleic acid, receptor-mediated endocytosis (see, e.g., Wu and Wu, 1987, J. Biol. Chem. 262:4429-4432), construction of a nucleic acid as part of a retroviral or other vector, etc. Methods of introduction of a nucleic acid include intradermal, intramuscular, intraperitoneal, intravenous, subcutaneous, intranasal, epidural, and oral routes. The nucleic acid may be administered by any convenient route, for example by infusion or bolus injection, by absorption through epithelial or mucocutaneous linings for example, oral mucosa, rectal and intestinal mucosa, and may be administered together with other biologically active agents. Administration can be systemic or local.

The peptides of the present invention appear to stimulate axon regeneration and stimulate cell survival. The terms "stimulate" and "promote" are used interchangeably herein. The ability of a peptide that comprises the tetrameric structural unit defined above to stimulate axon regeneration or to stimulate cell survival may be determined readily by any appropriate test, many suitable techniques being known. Examples of suitable tests are given in the Examples.

Briefly, the ability of a peptide of the invention to stimulate axon regeneration may be determined by an in vitro neurite outgrowth assay. In such an assay typically a coculture assay, a feeder layer, for example, of fibroblasts is established, neurones are plated on the feeder layer and are cultured in the presence and absence of the compound under investigation. Any suitable neurones may be used, for example, cerebellar granule cell neurons, hippocampal, dorsal root ganglion, olfactory, motor, or dopaminergic neurones. Neurite length is then measured, generally by microscopy after staining, and thus the effect of the compound under investigation on neurite outgrowth and hence axon regeneration is determined. The neurons may be of any appropriate origin. A growth factor known to stimulate neurite outgrowth, for example, FGF2 or NGF may be used as a control.

The ability of a peptide of the invention to stimulate cell survival may be assessed by determining the effect of the peptide on cells maintained under conditions under which they die or unless provided with a supplement. For example, many types of cell will die if maintained in a serum-free growth medium unless the medium is supplemented with an appropriate agent that stimulates their survival, for example, a growth factor. The nature of the agent may differ with cell type. For example, FGF stimulates the survival of fibroblasts in a serum-free medium. FGF is also effective in stimulating neurone survival.

Accordingly, in one suitable assay the effect of a peptide of the present invention on cell survival may be assessed by maintaining cells in a medium in which they will die unless the medium is supplemented with an agent that stimulates their survival, and determining the effect on cell survival of supplementation of the medium with the peptide. A growth factor known to stimulate survival of that type of cell may be used as a control, for example, FGF or insulin may be used for fibroblasts and for neurones.

Cell survival may be assessed by a biochemical assay, for example, by determining cell respiration, for example, by using the mitochondrial substrate MTS, which is [3-(4,5-dimethylthiazol-2-yl)-5-(3-carboxymethoxyphenyl)-2-(4-sulphophenyl)-2H-tetrazolium, inner salt] and measuring optical density at 490 nm. Alternatively or in addition, cell survival may be assessed by determining the number of viable cells, or may be assessed morphologically, for example, after fixing the cells and, if desired, staining to visualise the cytoskeleton, for example, with TRITC-conjugated falloidin.

As mentioned above, the peptides of the present invention appear to lack the mitogenic and apoptotic properties shown by many conventional growth factors. This is a clear advantage as the risk of tumorigenesis and of apoptosis mitigates against the therapeutic use of growth factors.

A peptide may be tested for mitogenic activity by any appropriate assay. Many suitable assays are well known.

Increase in the number of cells cultured in the presence of an agent compared with the number cultured in it absence is a simple test. A widely used test for mitogenesis involves the use of bromodeoxyuridine (BrDU), which is incorporated into the nucleus of cells entering the S phase of the cell cycle and hence is indication of the stimulation of mitosis. Cells are cultured in the presence of BrDU and in the presence and absence of a substance under investigation. The cells are then stained using BrDU. The presence of BrDU staining indicates stimulation of mitosis and hence that the agent under investigation is mitogenic. A known mitogen, for example, FGF2, may be used as a control.

The following non-limiting Examples illustrate the invention.

EXAMPLES

Example 1

General Methods for the Production of Peptides

Peptides are prepared by solid phase synthesis using standard Fmoc chemistry. This is based on sequential addition of amino acid residues, the α-amino and side chain amino groups of which are protected by a Fmoc group, to the amino group of a linker attached to an insoluble resin support. After removal of the protecting group from the amino acid at the end of the growing chain using piperidine, the next protected amino acid is added, giving a peptide attached through its carboxy terminus to the resin via a linker. This procedure is repeated until the final product has been assembled. The product is then removed from the resin using trifluoroacetic acid.

To produce peptides having a C-terminal amide group, methylbenzhdrylamine is used and for peptides having a free (unblocked) carboxy terminus traditional Merrifield resins are used. Acetylation of the N-terminus for blocked peptides is perfomed by reacting the peptide resin with a solution of acetic anhydride in dichloromethane in the presence of di-isopropylethylamine after removal of the N-α-t-butoxycarbonyl by acidolysis using trifluoroacetic acid.

Peptide dendrimers (multiple antigenic peptides, MAP) are prepared by standard procedures. For example, lysine having its a-amino and side chain amino groups protected with an F-moc group is coupled to a standard resin via a standard linking group as above. The protecting groups are removed by piperidine and further similarly protected lysines are added, one to the α-amino group and one to the side chain amino group. This results in a triple lysine backbone with four F-moc protecting groups, that is to say, a four branch MAP core. If desired, another F-moc protected lysine can be added to each of the four amino groups of the previous product, giving an eight branch core.

To a four branch core prepared as described above, the amino acids of the desired peptide are added sequentially from the C-terminus, see FIG. 5.

Cyclic peptides may be produced by synthesising linear peptides synthesised as described above with a cysteine residue flanking each end of the peptide sequence. The cysteine is coupled first to the resin followed by the other amino acids and finally by a cysteine at the N-terminus. The product is then cyclised by reacting the two side chain thiol groups with a 10% solution of iodine in methanol to form a disulphide bridge.

The peptides used in the Examples below were manufactured by Mimotopes (UK) Limited.

Example 2

Production of Peptide A(d)

Peptide A(d) has the structure [{Ac-DRVEPYSSSTA}$_2$-K]$_2$-K-OH, that is to say, four units of the acetylated peptide DRVEPYSSTA [SEQ.ID.NO.:14] are linked to a branched lysine tetramer backbone structure. The branched lysine backbone structure is prepared as described in Example 1 above. Peptide A(d) is also referred to herein as Ac-DRVE-PYSSSTA[lys]2[lys].

The F-moc protective groups are removed from the four lysine amino groups of the backbone structure, then alanine is added followed by threonine, serine, serine, tyrosine, proline, glutamic acid, valine, arginine, and aspartic acid.

Example 3

Production of Cyclic Peptide

The linear peptides DRVEPYSSTA [SEQ.ID.NO:14] is synthesised as described above may be prepared but with a cysteine residues flanking each end of the peptide sequence, giving the peptide CDRVEPYSSTAC [SEQ.ID.NO.:18]. The cysteine is coupled first to the resin followed by the other amino acids and finally by a cysteine at the N-terminus. The linear peptide is then cyclised by reacting the two side chain thiol groups with a 10% solution of iodine in methanol to form a disulphide bridge.

Example 4

Axon Regeneration

The ability of an exogenous factor to stimulate neurite outgrowth (axon regeneration) can be tested in a neurite outgrowth assay in vitro. The assay of choice should so simulate the in vivo conditions that the results are indicative of potential in vivo activity of the agents tested. The stimulating activity of a test agent can be compared with that of known neurite outgrowth-stimulating agents such as NGF and FGF2.

An example of such an assay is a co-culture assay in which neurons are cultured on top of cellular monolayers for 16 hours, before being fixed and stained with a neuron-specific antibody. The mean length of the longest neurite per cell can then be determined by fluorescence microscopy using an appropriate image analysis programme. The neurons may be, for example, (in this case cerebellar granule cell neurons, hippocampal, dorsal root ganglion, olfactory, motor or dopaminergic neurons. The cellular monolayer is, for example NIH 3T3 fibroblasts.

The effect of various peptides of the invention on axon regeneration was determined using the following in vitro neurite outgrowth assay.

General Method

Monolayers of NIH 3T3 fibroblasts were established by seeding 80,000 cells per well in Lab-Tek 8-chamber slides previously coated sequentially with poly-L-lysine and fibronectin and culturing them overnight in DMEM+10% FCS growth medium.

Cerebellum was dissected from post-natal day 2-4 rat pups and the meninges and extraneous tissue discarded. Cerebellum was chopped into small pieces and trypsinised for 10 minutes at 37° C. Trypsin was neutralised using growth medium and the cells pelleted at 1000×g for 7 minutes. Cerebellar neurons were then resuspended in SATO growth medium containing 2% FCS, counted, and plated on top of the fibroblast monolayer at a density of 1,500 neurons per well. After 16 hours, cocultures were fixed with 4% para-formaldehyde and stained with an anti-GAP43 neuron-specific antibody, which was a gift from Dr Graham Wilkin, Imperial College Department of Biochemistry, London, but any other neuron-specific marker can be used.

The mean neurite length of 150-200 neurons per well was determined using a fluorescent microscope and Zeiss KS300 imaging software.

Example 4a

Method

Peptides A, A(d), B, C, D, E, and F were each incorporated in the SATO medium at a range of concentrations from 0 to 200 μg/ml. Nerve growth factor (NGF) and fibroblast growth factor (FGF2) were used as controls at the same range of concentrations.

Results

All of the peptides tested stimulate an 80-120% increase in neurite length (axon regeneration) of the rat cerebellar granule neurons cultured on monolayers of fibroblasts (NIB 3T3 cells). This response at least equals, and usually surpasses, the response of those neurons to nerve growth factor (NGF) and fibroblast growth factor (FGF) in the same assay.

In this neurite outgrowth assay, the peptide concentrations giving maximal effects are:

|            | μg/ml    | μM       |
|------------|----------|----------|
| Peptide A  | 100-200  | 100-200  |
| Peptide A(d)| 1.5-2.5 | ~0.4     |
| Peptide B  | 75       | 150      |
| Peptide C  | 38       | 75       |
| Peptide D  | 63       | 100      |
| Peptide E  | 50-100   | 50-100   |
| Peptide F  | 100      | 100      |

Example 4b

In the neurite outgrowth assay described in the General Method above, the mean neurite length approximately doubles over the 16 hour culture period when a neurite outgrowth-stimulating factor is included in the co-culture medium. Such factors include NGF, FGF2, soluble NCAM.

Figure 1B:
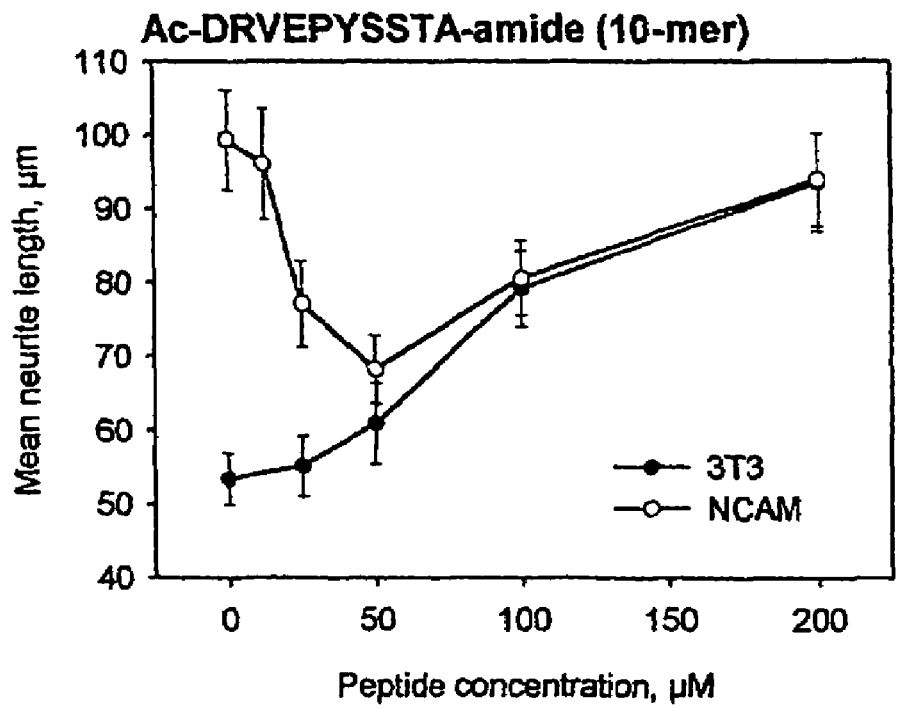
Figure 1C:
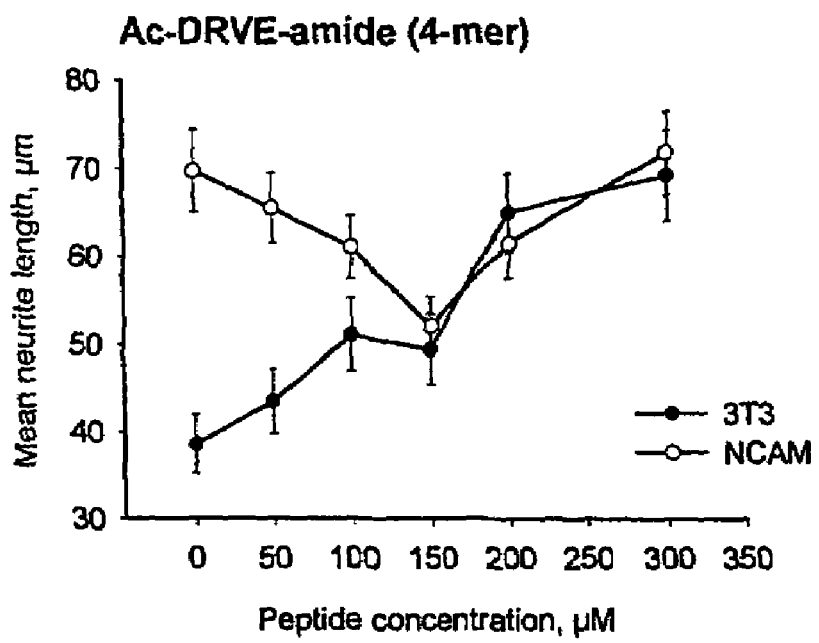
Figure 1D:
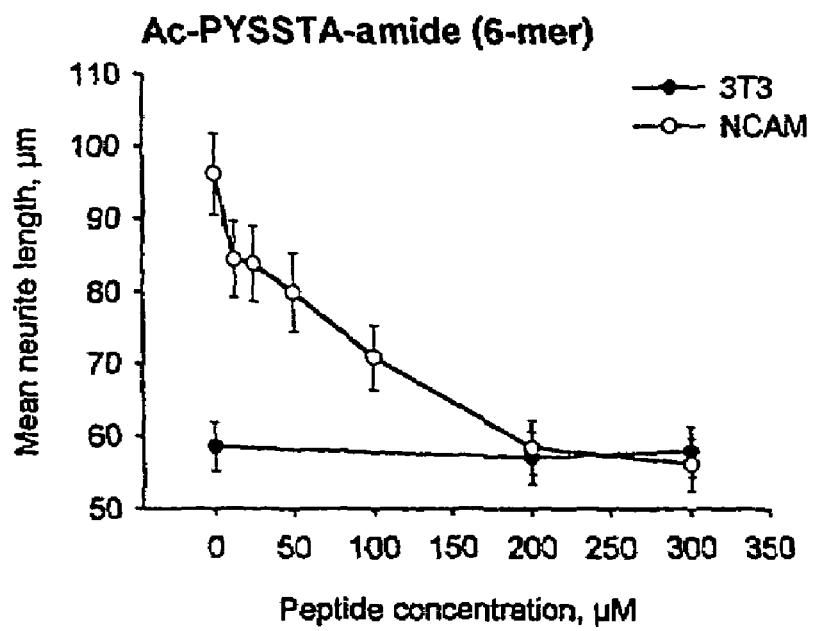

When a synthetic 13 amino acid peptide, Ac-SIDRVE-PYSSTAQ-amide, derived from the first fibronectin type III domain of NCAM, was included in the coculture medium, a dose-dependent increase in neurite outgrowth was seen, until at 100 μM the neurite length equalled that stimulated by the known neurite outgrowth-stimulating molecule NCAM (FIG. 1a). The full activity was retained in the 10 amino acid peptide Ac-DRVEPYSSTA-amide (FIG. 1b), and even the 4 amino acid peptide Ac-DRVE-amide could stimulate the response (FIG. 1c). The graphs show that at low concentrations the peptides inhibit neurite outgrowth stimulated by NCAM, but at higher concentrations, they are themselves able to mimic NCAM-stimulated neurite outgrowth. A peptide with the sequence Ac-PYSSTA-amide was able to inhibit NCAM-stimulated neurite outgrowth, but was itself unable to stimulate neurite outgrowth (FIG. 1d).

Figure 1E:
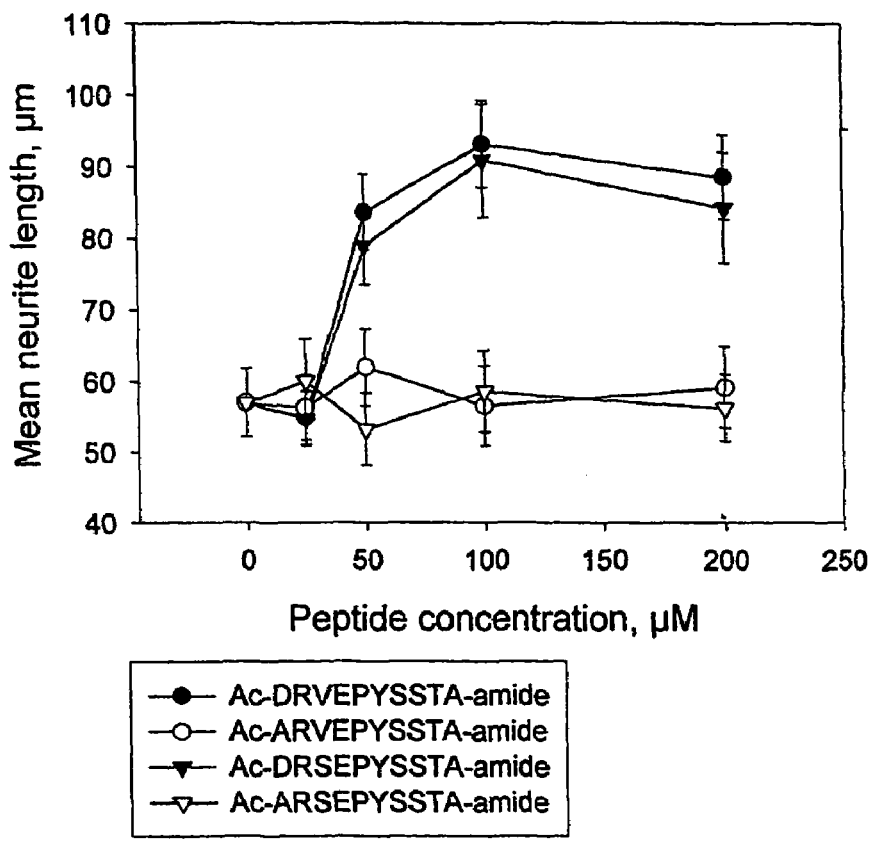

By introducing amino-acid substitutions into the 'parent' DRVEPYSSTA sequence, the importance of various amino acids can be seen. Thus Ac-DRSEPYSSTA-amide and Ac-DAVEPYSSTA-amide retain the full ability to stimulate neurite outgrowth, while Ac-ARVEPYSSTA-amide and Ac-ARSEPYSSTA-amide do not see FIG. 1e. However, it was predicted that multimeric versions of even those peptides which do not stimulate neurite outgrowth as monomers would have neurite outgrowth-stimulating activity, since the evidence, see below, suggests that these peptides bind and activate FGF receptors.

Figure 1F:
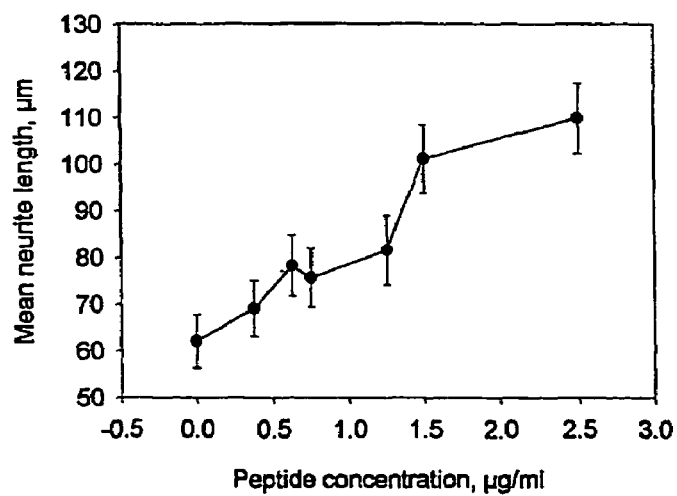
Figure 1G:
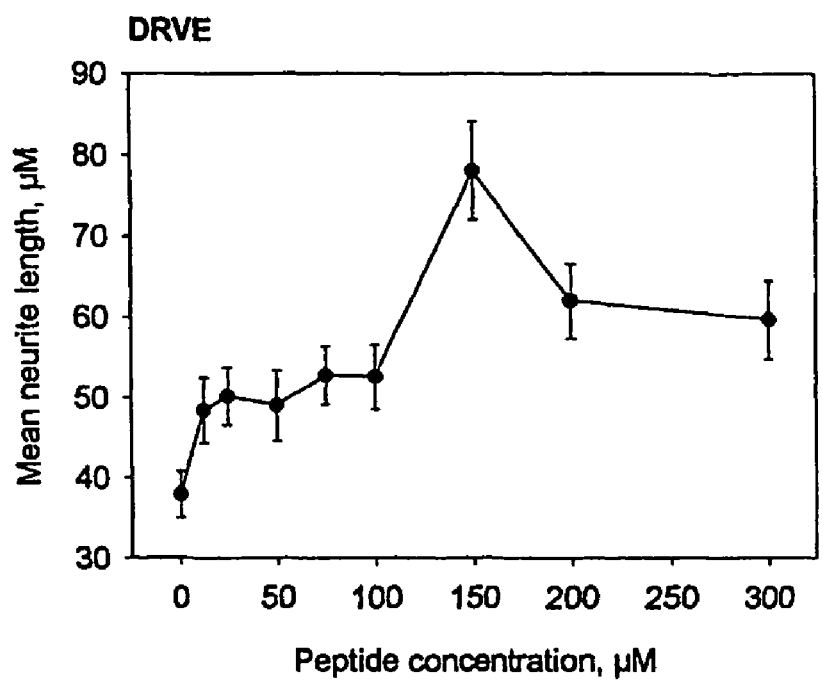
Figure 1H:
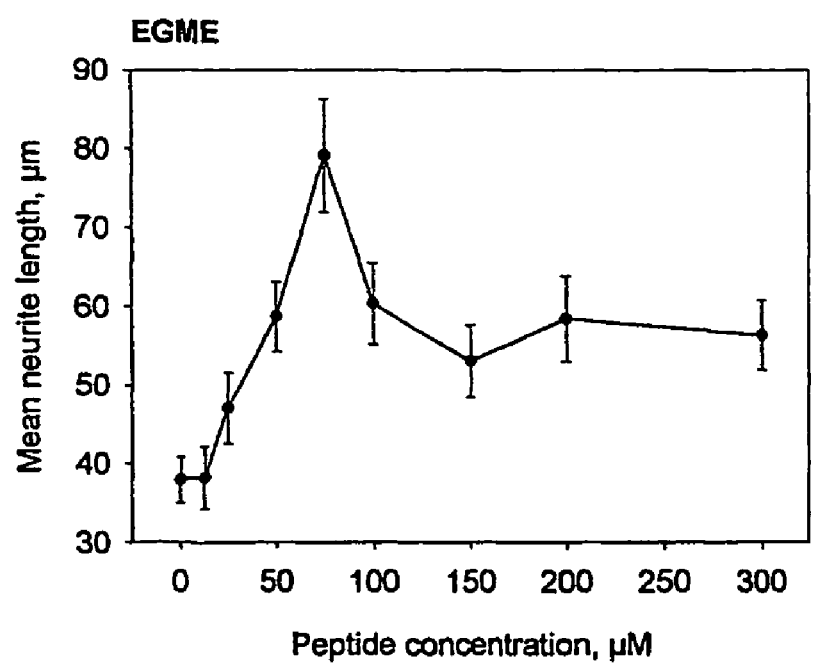

A peptide Ac-EGME-amide stimulates neurite outgrowth to the same extent as Ac-DRVE-amide (FIG. 1g,h). A peptide EGMEGM is equally active. A multimeric peptide, Ac-DRVEPYSSTA[lys]$_2$[lys]-OH, consisting of four copies of the peptide linked to a triple-lysine backbone ie [{Ac-DRVEPYSSTA}$_2$-K]$_2$-K-OH, Peptide A(d), was found to stimulate neurite outgrowth with 250 times more potency than the monomeric peptide, stimulating maximal neurite outgrowth at 400 nM and with a bi-phasic dose-response curve (FIG. 1f).

All the evidence shows that these peptides are binding to and activating FGF receptors to stimulate neurite outgrowth.

Figure 1I:
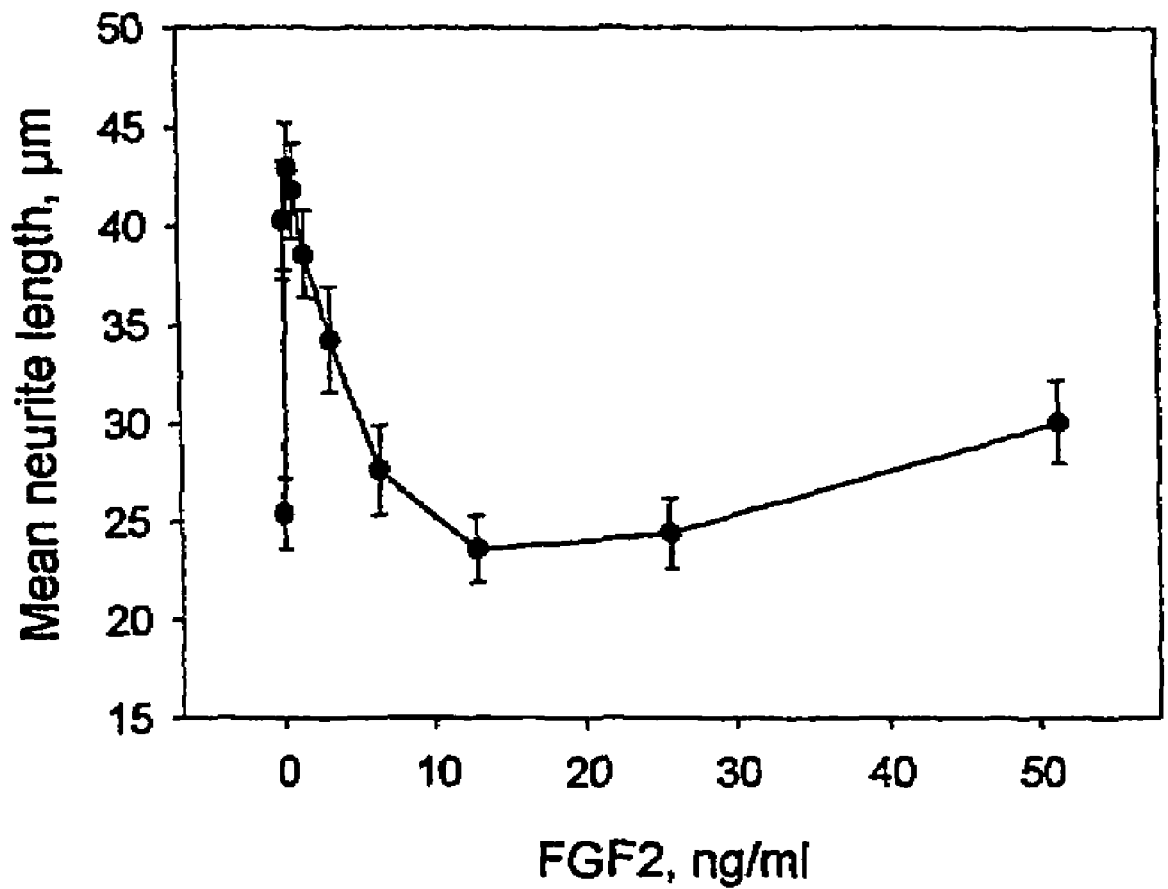
Figure 1J:
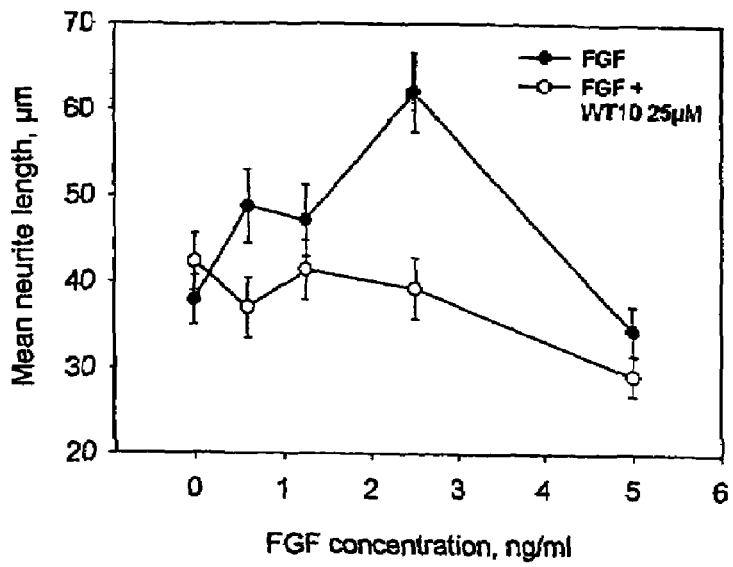
Figure 1K:
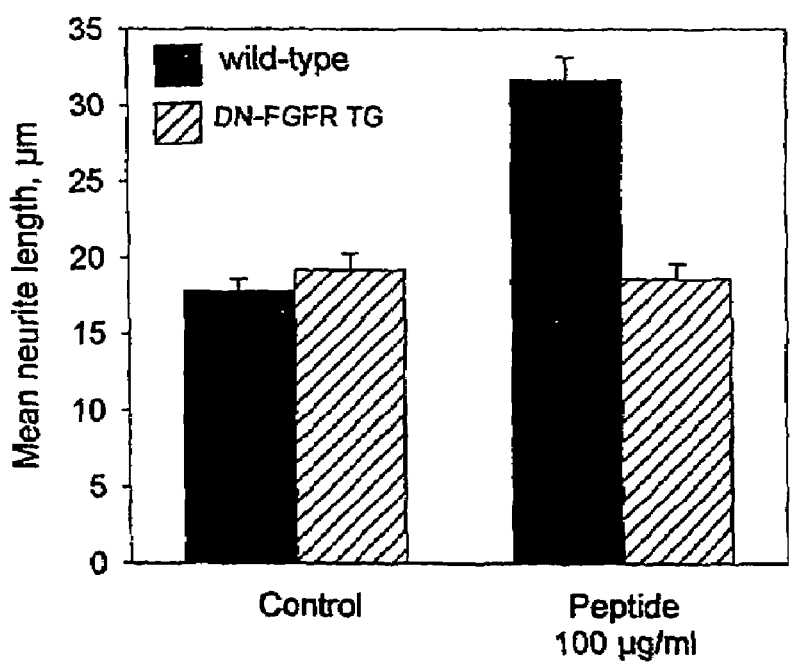

FGF2 stimulates neurite outgrowth in this assay with a biphasic dose-response curve (FIG. 1i). Low concentrations of the monomeric 10-mer Ac-DRVEPYSSTA-amide (25 μM) inhibit neurite outgrowth stimulated by FGF2 (FIG. 1j). Cerebellar neurones taken from transgenic mice expressing a dominant-negative form of FGF receptors such that they are unable to signal through the FGF receptor are unable to extend neurites in response the monomeric 10-mer peptide Ac-DRVEPYSSTA-amide (FIG. 1k). This shows that FGF receptors are required for the neurite outgrowth effect of the peptide Ac-DRVEPYSSTA-amide and demonstrates that the peptides of the invention bind to and activate FGF receptors.

Example 5

Promotion of Cell Survival

The ability of an agent to stimulate cell survival in vivo, i.e. to prevent cells from undergoing premature apoptosis, can be predicted by its ability to stimulate cell survival in vitro in a defined cell survival assay. A suitable assay is one in which cells are plated at low density in serum-free medium for a number of days, one, two or three, for example, during which time they die unless the medium is supplemented with a survival factor. In such an assay, the activity of the test agent can be compared with that of known survival factors such as insulin.

Example 5a

Survival of Fibroblasts

The Ability of Peptide A(d) to Stimulate Survival of 3T3 Fibroblasts was Demonstrated in the Following Assay.

Method

NIH 3T3 fibroblasts were plated in each well of a 96-well microtitre plate at a density of 7,000 cells per well in DMEM containing 3% FCS and left to attach overnight. The following day the growth medium was removed and replaced with 0.1 ml DMEM supplemented with FGF or Peptide A(d) or both, eight wells for each condition. The negative control was DMEM alone (maximal cell death) and the positive control was supplementation with 0.5% FCS (maximal cell survival).

Six days later (seven days from first plating the cells), the relative number of living cells in each well was assessed by adding the mitochondrial substrate MTS, [3-(4,5-dmethylthiazol-2-yl)-5-(3-carboxymethoxyphenyl)-2-(4-sulphophenyl)-2H-tetrazolium, inner salt), for four hours before reading the optical density on a microtitre plate reader at a wavelength of 490 nm. The optical density gives a measure of the number of respiring cells present in each well at the end of the assay period.

In addition to the biochemical assay, survival was assessed qualitatively using a morphologic method in which cells were plated in 8-chamber Lab Tek slides in DbEM alone (negative control), or DMEM supplemented with 0.5 ng/ml FGF2; 0.5% FCS (positive control), or 25-200 µg/ml Peptide A(d). After three days the cells were fixed with 4% paraformaldehyde, permeablised with methanol and stained with TRITC-conjugated falloidin to visualise the cell cytoskeleton.

Results

When 3T3 fibroblasts are maintained at low density in serum-free DMEM, they die unless the medium is supplemented with an agent stimulating their survival. FGF is such a survival factor for 3T3 fibroblasts. When Peptide A(d) was added to the fibroblast culture medium alone at 25 µg/ml it stimulated the survival of 3T3 fibroblasts to the same extent as 0.125 ng/ml FGF2. When DMEM was supplemented with Peptide A(d) together with FGF2, cell survival was greater than with either agent alone.

Discussion

The effects of Peptide A(d) on cell survival were very striking. All concentrations were at least as good as the positive control, 0.5% FCS, at stimulating survival. In this experiment, there were far fewer cells remaining in the presence of FGF than in the presence of the peptide.

Example 5b

Survival of Neurons

Using the same survival assays as those described above Peptide A(d) has been shown to stimulate survival of cerebellar neurons.

Example 6

Stimulation of Cell Survival

Method

NIH 3T3 cells are plated in 96-well plates at a density of 5,500 cells/well in 100 µl DMEM containing 0.5% FCS. After 24 hours, this medium is aspirated from the wells and replaced with 100 µl serum-free DMEM alone, or supplemented with 0.5% FCS (positive control), or a single potential survival factor, with four identical wells set up for each condition. The cells are left for up to seven days at 37 degrees and 8% $CO_2$ before the cell survival is determined using an MTS assay. In this assay 20 µl of MTS substrate is added to each 100 µl well and the plate left in the incubator for up to four hours. Respiring cells produce a coloured reaction product that can be read using a spectrophotometer at 490 nm. The coloured reaction product and hence the absorbance at 490 nm increases in proportion to the number of living (respiring) cells in the well. The mean absorbance at 490 nm+/−SEM is determined for the four identically set up wells. Wells containing a known survival factor such as insulin will contain more living cells after three days than cells cultured in unsupplemented medium.

Results

In the survival assay described above, FGF2 (very low concentrations—see later) and insulin stimulate dose-dependent survival of NIH3T3 cells in serum-free conditions. The results obtained using FGF2 are shown in FIG. 2a,iii and the results using insulin in FIG. 2a,i.

The 4-branched peptide Ac-DRVEPYSSTA[lys]2[lys] i.e. [{Ac-DRVEPYSSTA}$_2$-K]$_2$-K-OH, Peptide A(d), stimulates dose-dependent survival fully mimicking and indistinguishable from survival stimulated by insulin and FGF2, and is able to stimulate survival in serum-free conditions for at least seven days (maximum time tested) (FIG. 2a,ii).

Figure 2B:
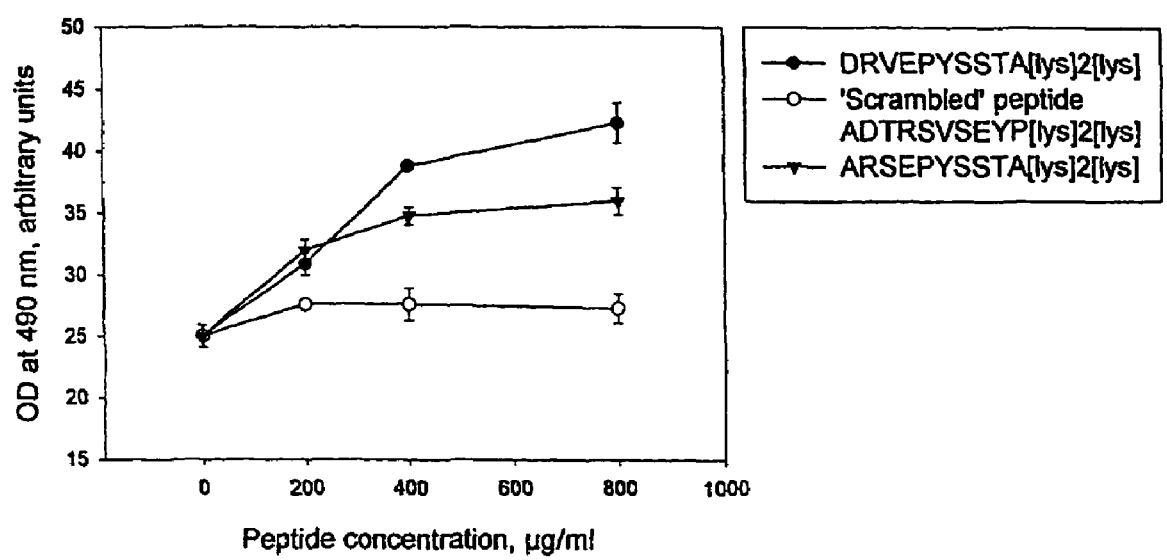

A 'scrambled' version of this peptide, namely Ac-ADTRSVSEYP [lys]2[lys] i.e. [{Ac-ADTRSVSEYP}$_2$-K]$_2$-K-OH, was ineffective, but a "mutated" peptide with D/V and V/S amino acid substitutions, namely Ac-ARSEPYSSTA [lys]2[lys] i.e. [{Ac-ARSEPYSSTA}$_2$-K]$_2$-K-OH stimulated cell survival, though not as potently as the parent peptide Ac-DRVEPYSSTA[lys]2[lys] (FIG. 2b). This shows that peptides which do not stimulate neurite outgrowth as monomers are nonetheless able to stimulate cell survival and should also stimulate neurite outgrowth as multimers. Peptides such as PYSSTA therefore, which do not appear to stimulate neurite outgrowth themselves, and peptides containing the PYSSTA motif will also be able to stimulate neurite outgrowth and cell survival as multimers.

Figure 2C:
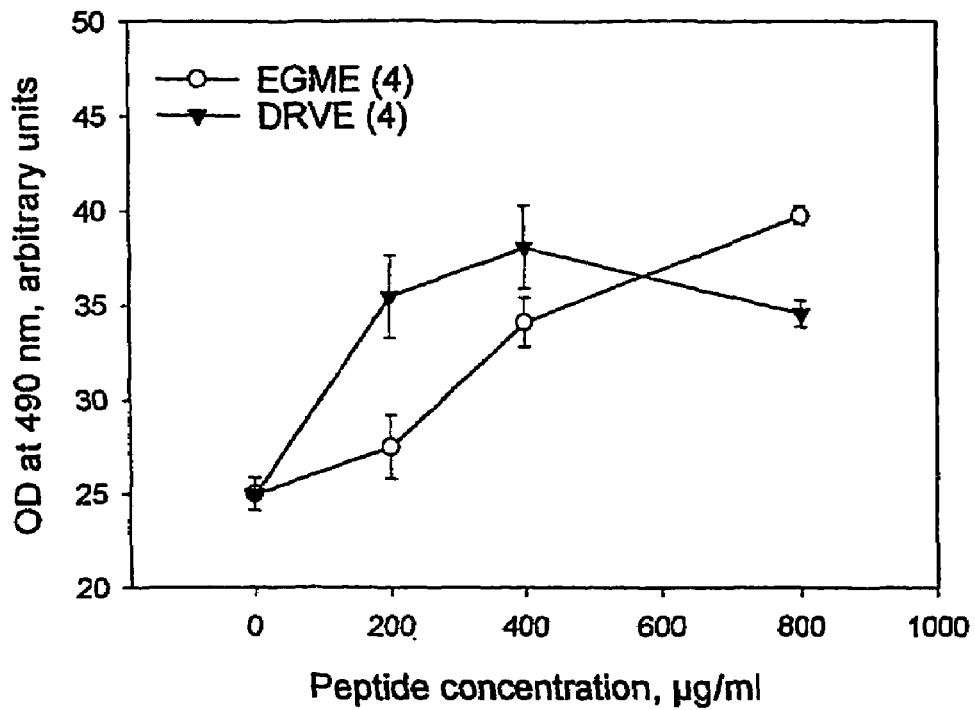
Figure 2D:
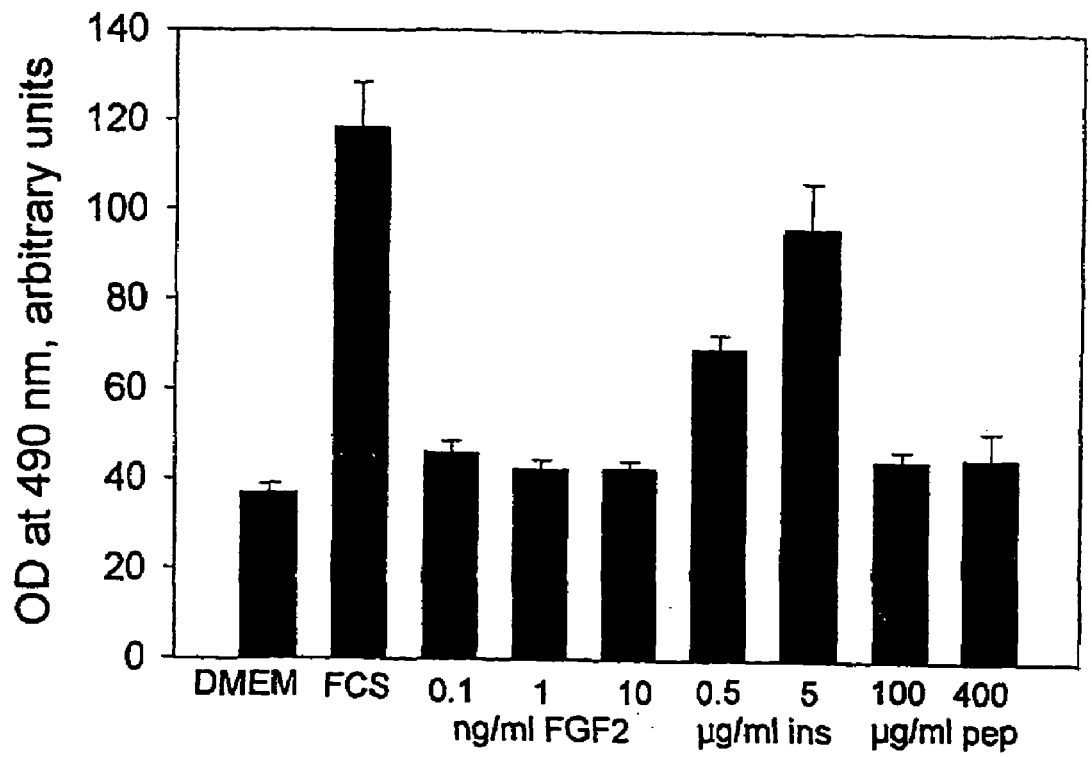

The monomeric peptides DRVE and EGME in the form Ac-DRVE-amide and Ac-EGME-amide were able to stimulate cell survival (FIG. 2c), in an effect equivalent to that of the dendrimeric Peptide A(d). The evidence shows that all these peptides act by binding and activating FGF receptors, since the peptide and FGF are specifically unable to stimulate the survival of a cell line which lacks FGF receptors, the L6 cell line (FIG. 2d). FIG. 2d compares the effects of DMEM, FCS, FGF2 at 0.1, 1 and 10 ng/ml, insulin at 0.5 and 5 µg/ml, and Peptide A(d) at 100 and 400 µg/ml.

Although low concentrations of FGF2 stimulate survival of NIH3T3 cells, higher concentrations (1 ng/ml) are ineffective and 10 ng/ml stimulates apoptosis in these low-density cultures, i.e. after three days culture in the presence of DMEM supplemented with 10 ng/ml FGF2 there are fewer cells remaining than in wells containing unsupplemented DMEM (FIG. 2e,i). This apoptotic effect of FGF2 can be reversed by further supplementing the 10 ng/ml FGF-containing wells with PD, an inhibitor of MAP kinase signalling (FIG. 2e,ii).

Further Examples of Stimulation of Cell Survival

A Western blot (FIG. 2f) was obtained as follows: one million NIH 3T3 cells were serum starved for 24 hours then challenged with the following agents: DMEM, 10% FCS, 0.1 ng/ml FGF2, 1 ng/ml FGF2, 10 ng/ml FGF2, 5 µg/ml insulin, 400 µg/ml peptide 52 for 10 minutes at 37 degrees Celcius before being lysed in sample buffer and band separated by PAGE. Proteins were transferred to PVDF membranes and probed with an antibody that recognises tyrosine phosphorylated MAP kinse (upper panel). Triggering with 10% FCS, and 1 or 10 ng/ml FGF2 resulted in MAP kinase activation, while insulin showed a small activation and 0.1 ng/ml FGF2 and 400 µg/ml peptide did not. The membrane was stripped of antibody and re-probed with a MAP kinase antibody which does not discriminate between phosphorylated and non-phosphorylated MAP kinase (lower panel). This shows that the amount of MAP kinase was the same in all lanes.

Figure 2F:
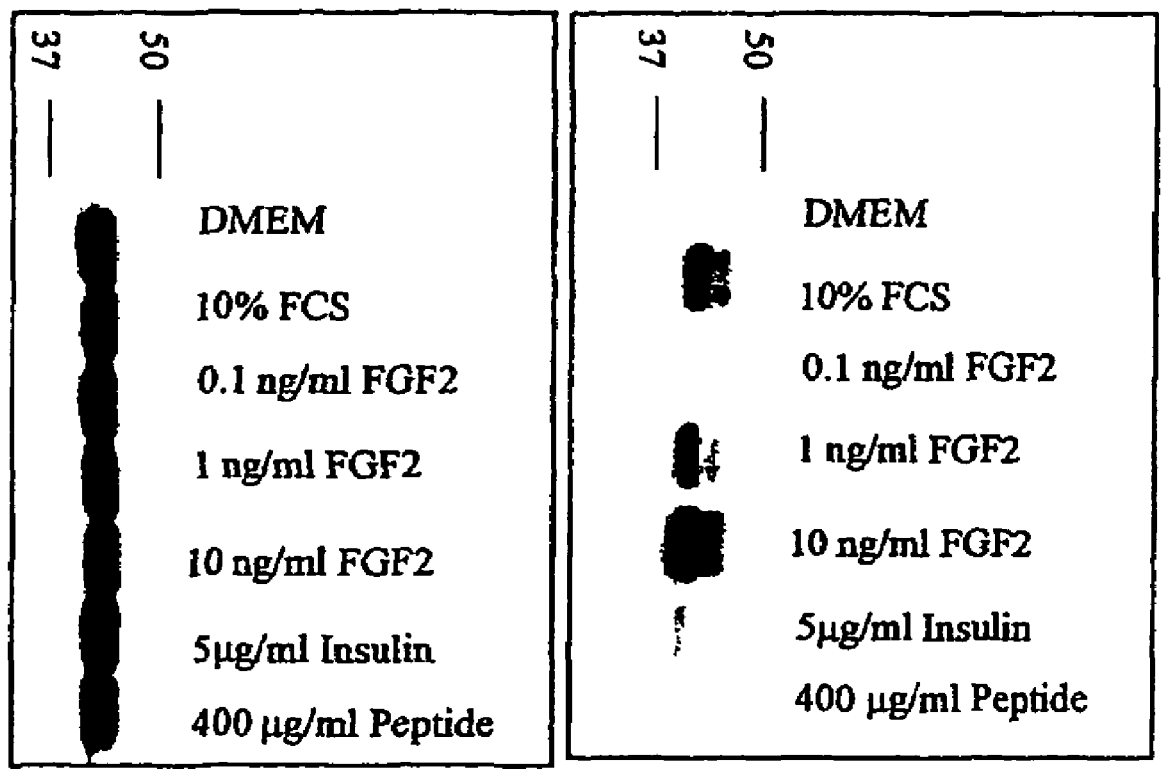

The results shown in FIG. 2f demonstrate that FCS, 1 and 10 ng/ml FGF2 stimulate MAP kinase activation, while 0.1 ng/ml FGF2, peptide A(d) i.e. Ac-DRVEPYSSTA[lys]2[lys], and insulin do not. Thus the peptide mimics the effects of low concentrations of FGF2, namely stimulation of neurite outgrowth and cell survival, but not the apoptotic effect of higher concentrations of FGF2.

Figure 2G:
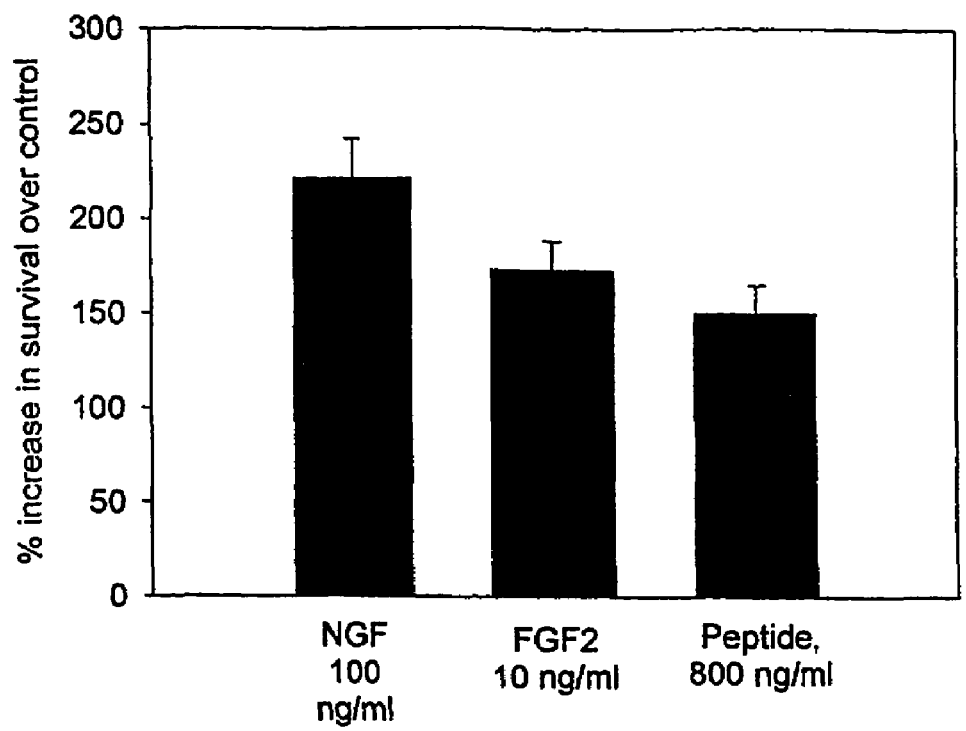

The effect of Peptide A(d) on the survival of DRG neurons was demonstrated as follows. DRG neurons were taken from embryonic day 16 rates and cultured at a density of-10,000 cells/well of a 96-well plate-over 10 days in SATO medium, unsupplemented or supplemented with 10 ng/ml NGF, 10 ng/ml FGF2 or 800 ng/ml Peptide A(d). An OD of 100% reflects the baseline cell survival n the absence of any supplement in the medium. FIG. 2g shows that NGF at 10 ng/ml increases cell survival by 121%, while FGF2 at 10 ng/ml increases survival by 73%, and the peptide A(d) at 800 ng/ml increases survival by 51%.

NIH 3T3 cells were cultured for three days in the presence of DMEM alone, or supplemented with insulin at 0.5 pg/ml, FGF2 at 0.1 and 1 ng/ml, or Peptide A(d) at 10 ng/ml. Cells were then fixed and actin filaments visualised using TRITC-conjugated phalloidin to show the 3T3 morphology.

Figure 2H:
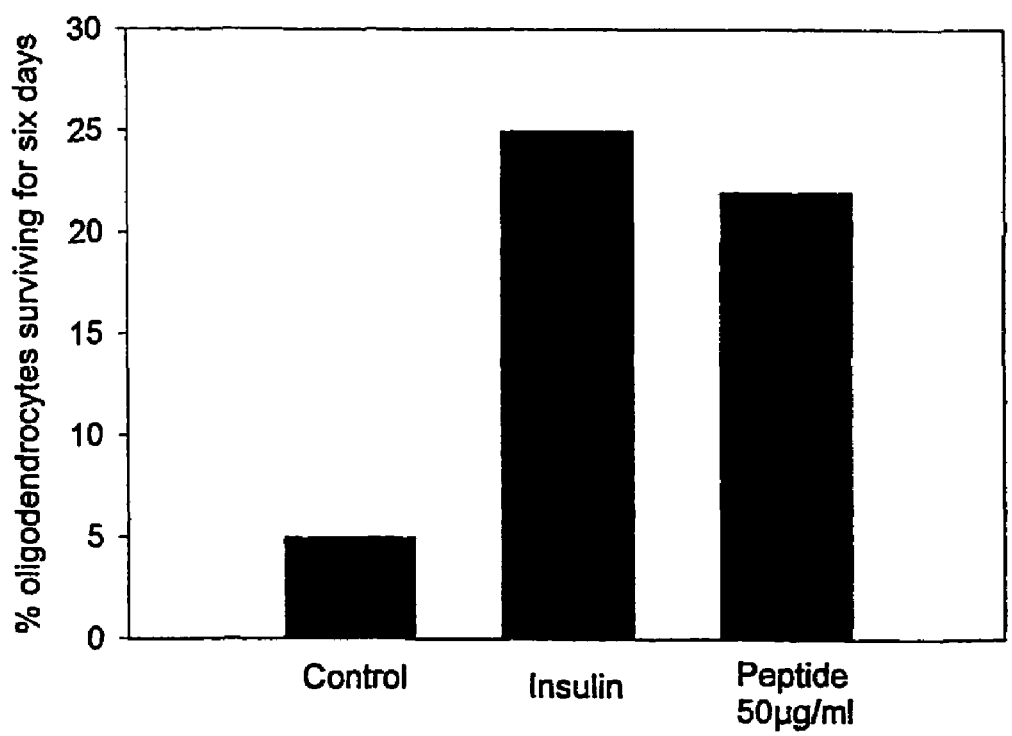
Figure 2I:
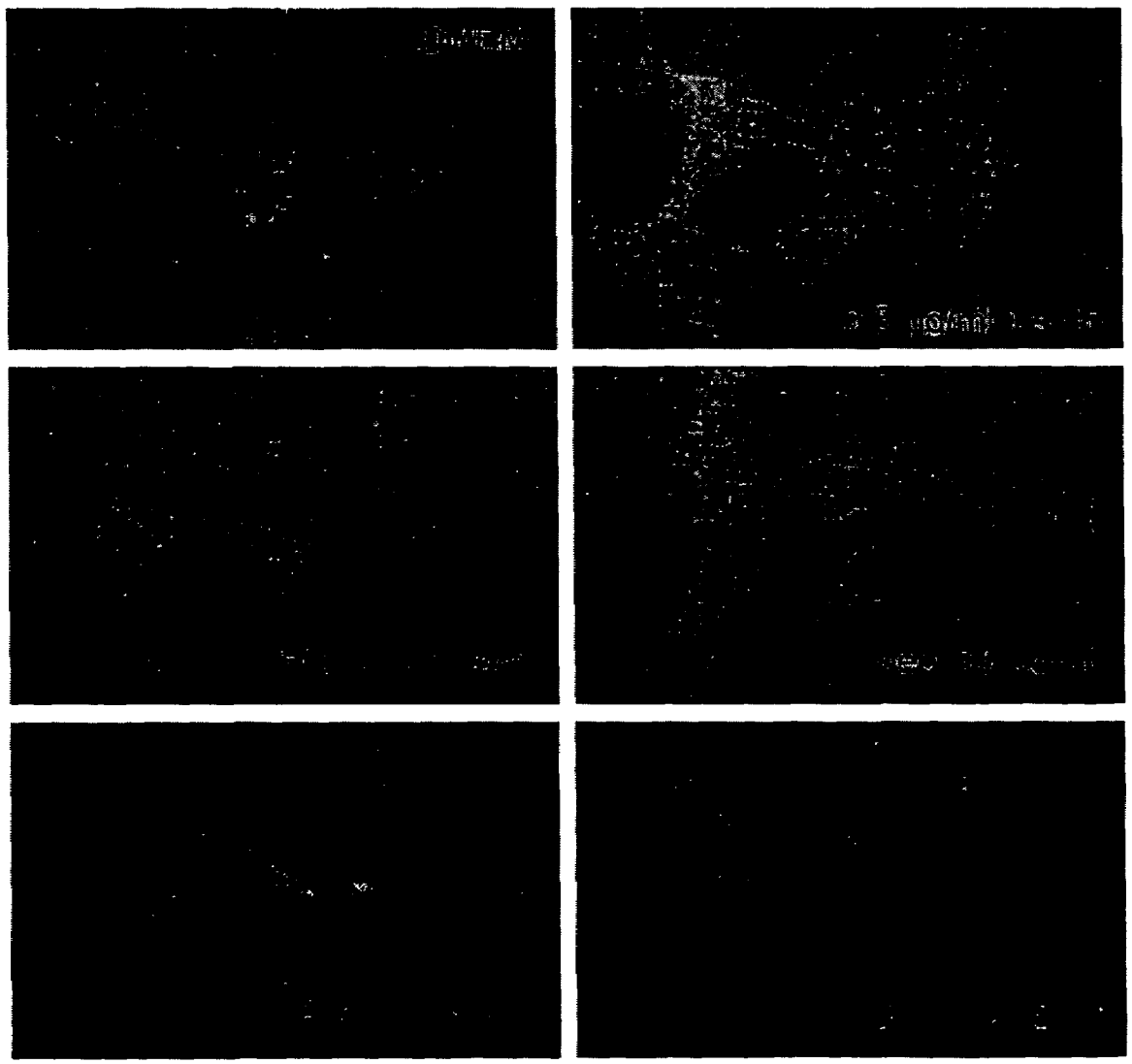

Cells do not survive well in the absence of supplements i.e. in DMEM alone. In contrast, supplementation with insulin, low concentrations of FGF2 (0.1 ng/ml) or Peptide A(d) stimulate cell survival. The morphology of the cells in the presence of these agents is indistinguishable. In the presence of higher concentrations of FGF2 (1 and 10 ng/ml), the cells are reduced in number, and appear apoptotic, with bright and rounded morphology. These results are shown in FIG. 2i.

Example 7

Oligodendrocyte Survival

Oligodendrocytes are the myelinating glia of the central nervous system. They can be cultured in vitro, but require the inclusion of certain survival factors in the growth medium in order to survive in vitro. One such survival factor is insulin. Purified cultures of oligodendrocyte precursors provide an in vitro assay system in which to test for agents which stimulate oligodendrocyte survival, and may be expected to be beneficial for stimulating oligodendrocyte survival in vivo in conditions of demyelination, e.g. multiple sclerosis.

Method

Oligodendrocyte progenitors (O4 positive) are purified from postnatal day 4 rat cerebral cortex. First a trypsinised preparation of cortical cells is dissociated to single cell suspension and pre-plated to remove unwanted adherent cells such as microglia and macrophages. Oligodendrocyte progenitors express the O4 antigen, and can be purified by panning on petri-dishes coated with anti O4 antibodies. Unbound cells are removed by gentle washing, then O4 positive cells are removed by triturating them off the plate with DMEM containing 1% FCS, through a flame-polished pasteur pipette. O4 positive cells are plated on polyornithine-coated glass coverslips at a density of 500,000 cells per well in minimal growth medium containing insulin or the peptide Ac-DRVEPYSSTA[lys]2[lys] i.e. [{Ac-DRVE-PYSSTA}$_2$-K]$_2$-K-OH, Peptide A(d), for six days, before being fixed and stained with the anti O4 antibody. Viable O4 positive cells are counted for each condition Results FIG. 2h shows that after six days in culture in medium supplemented with insulin (positive control) 25% of the cells originally plated survive. When the medium is supplemented with the peptide A(d), a dose-dependent survival effect is seen, such that at 25 µg/ml 22% of the cells survive. This is comparable to the survival seen in the presence of insulin, a known survival factor for these cells.

Example 8

Peptide A(d) Does Not Stimulate Mitogenesis

FGF stimulates axonal regeneration, cell survival and mitogenesis. Peptide A(d) stimulates axonal regeneration and cell survival to a comparable degree. However, when cells are observed growing in the presence of FGF2 or Peptide A(d) it is clear that, unlike FGF2, Peptide A(d)-does not stimulate mitogenesis. This can be seen by the failure of Peptide A(d)-treated cells to show the rounding-up characteristic of cell division, and there is not the increase in cell number observed in the presence of a mitogenic stimulation by FGF2.

The following assays are used to quantitate any mitogenic effect of the peptide:

1. Standard Mitogenic Assay: A quiescent monolayer of 3T3 fibroblasts in serum-free DMEM is treated with FGF or Peptide A(d) in the presence of bromodeoxyturidine (BrDU) for four hours. After this time, cells are fixed and then stained for bromodeoxyuridine which is incorporated only into the nucleus of cells entering S phase of the cell-cycle, an indication of stimulation of mitogenesis. If the same number of cells incorporate BrDU in DMEM alone or supplemented with Peptide A(d) then the peptide does not stimulate mitogenesis. In the presence of FGF there should be a large increase in the number of cells incorporating BrDU as FGF is an established mitogen.

2. Cell count: 3T3 cells growing in DMEM/0.5% FCS are counted using a graticule before and after the medium is supplemented with Peptide A(d) or FGF2 for four days. Any increase in cell number observed in the presence of either agent will indicate a mitogenic effect.

Example 9

Mitogenesis

Figure 3A:
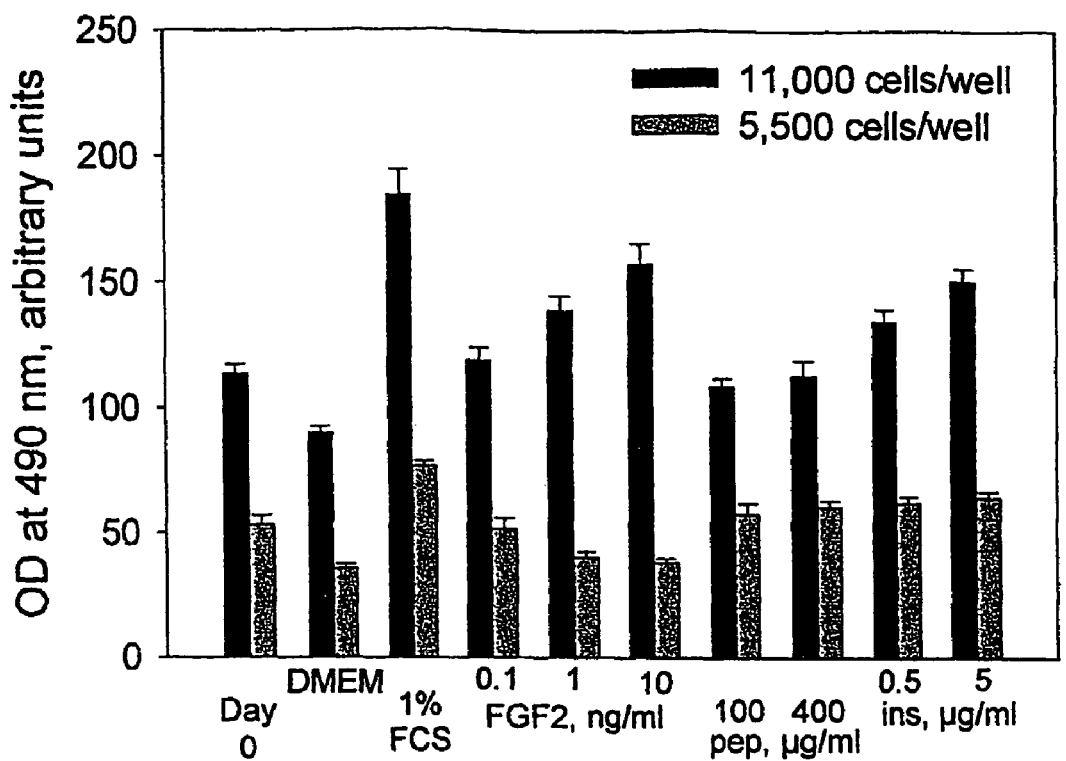
FIG. 3a shows the effects of Peptide A(d) on cell survival at two different cell plating densities, 5,500 cells/well and 11,000 cells/well, compared with that of FGF2 and insulin.

FGF2 is a mitogen for a range of cells, including NIH3T3 cells. When the cells are plated at low density (5,500 cells per well), 10 ng/ml FGF2 stimulates apoptosis. However, when the cells are plated more densely (11,000 cells per well), 10 ng/ml FGF2 stimulates cell proliferation (FIG. 3a), as does insulin. The peptide A(d) does not stimulate proliferation.

The mitogenicity of an agent can be determined by testing its ability to stimulate entry of cells into 'S' phase in readiness for cell division. This is done by standard methodology and involves incubating cells in the presence of a potential mitogen in DMEM supplemented with bromodeoxyuridine. After six hours the cells are fixed and stained with an antibody recognising bromodeoxyuridine. Cells in S phase can be distinguished by their incorporation of bromodeoxyuridine into DNA.

Figure 3B:
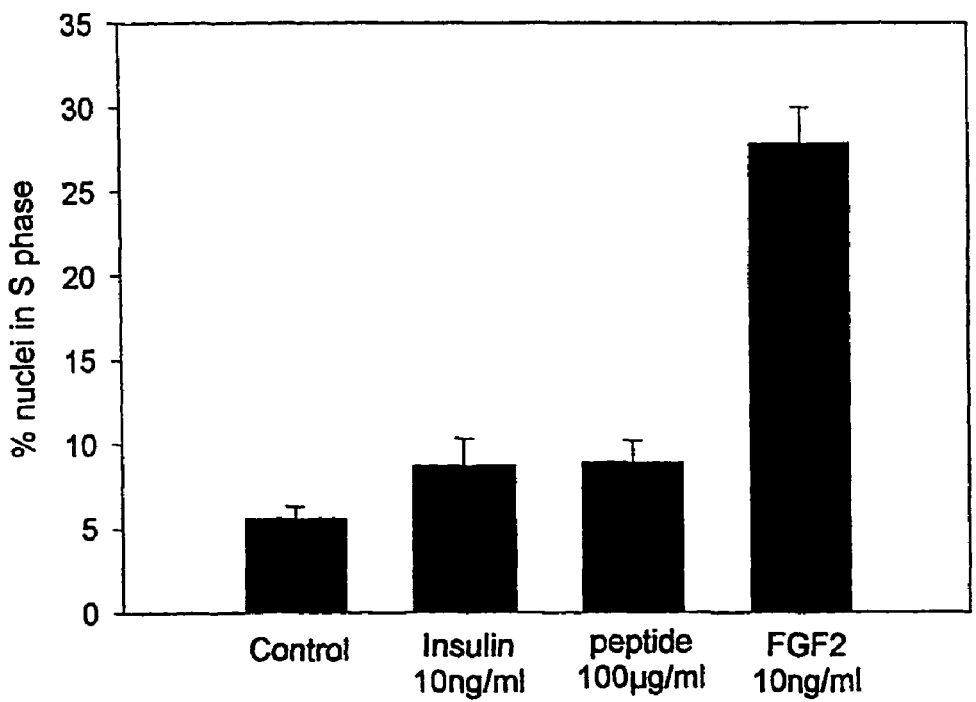
FIG. 3b shows the effects of insulin, Peptide A(d) and FGF2 on the incorporation of BrDU into cells, which is an indicator of mitogenesis.

In this assay, the mitogenicity of 10 ng/ml FGF2 can be seen, but the peptide A(d) again mimics low concentrations (0.1 ng/ml) FGF2 in being unable to stimulate entry into S phase (FIG. 3b). Thus FGF2 is a mitogen at high concentrations, but the peptide is not mitogenic at any of the concentrations tested. Thus as a trophic and neuritogenic therapeutic the peptide has advantages over FGF2 in terms of safety: use of FGF2 runs the risk of stimulating uncontrolled cell division and tumour formation.

The invention claimed is:

1. A purified peptide of from 10 to 30 amino acid residues, comprising the sequence DRVEPYSSTA (SEQ ID NO:14).

2. The peptide of claim 1, wherein said peptide has up to 25 amino acid residues.

3. The peptide of claim 2, wherein said peptide has up to 20 amino acid residues.

4. The peptide of claim 3, wherein said peptide has up to 15 amino acid residues.

5. The peptide of claim 4, wherein said peptide comprises the sequence CDRVEPYSSTAC (SEQ ID NO:18) or SIDRVEPYSSTAQ (SEQ ID NO:19).

6. The peptide of claim 1, wherein said peptide consists of the sequence DRVEPYSSTA (SEQ ID NO:14), CDRVEPYSSTAC (SEQ ID NO:18), or SIDRVEPYSSTAQ (SEQ ID NO:19).

7. A purified peptide of from 4 to 6 amino acid residues, comprising the sequence DRVE (SEQ ID NO:6).

8. The purified peptide of claim 7, consisting of the sequence DRVE (SEQ ID NO:6).

9. A purified peptide of from 10 to 30 amino acid residues, comprising the sequence DRVEPYSSTA (SEQ ID NO:14), wherein said peptide comprises an acetyl modification at the N-terminus, and an amide group modification at the carboxy terminus (Peptide A, modified SEQ ID NO:14).

10. A purified peptide of from 10 to 30 amino acid residues, comprising the sequence DRVEPYSSTA (SEQ ID NO:14), wherein said peptide is in multimeric form linked via one or more lysine residues, and has the structure [{Ac-DRVEPYSSTA}$_2$-K]$_2$-K-OH (Peptide A(d), modified SEQ ID NO:14), wherein Ac is an acyl group.

11. The peptide of claim 10, wherein said acyl group is a lower acyl group of from 1 to 4 carbon atoms.

12. A purified peptide of from 4 to 6 amino acid residues, comprising the sequence DRVE (SEQ ID NO:6), wherein said peptide comprises an acyl group modification at the N-terminus and an amide group modification at the carboxy terminus.

13. A method for stimulating the survival of, or neurite outgrowth in, cultured mammalian neuron, oligodendrocyte or fibroblast cells, comprising providing to said cultured cells a biologically-effective amount of a peptide in accordance with claim 1, claim 7, claim 9, claim 10, or claim 12, for a time sufficient to stimulate the survival of, or neurite outgrowth in, said cultured mammalian cells.

14. A method for stimulating neurite outgrowth in cultured mammalian neuron, oligodendrocyte or fibroblast cells comprising, providing to said cultured cells a biologically-effective amount of a purified peptide selected from the group consisting of:
  (a) a peptide of from 4 to 6 amino acid residues, comprising the sequence DRVE (SEQ ID NO:6);
  (b) a peptide of from 4 to 6 amino acid residues, comprising the sequence DRVE (SEQ ID NO:6), wherein said peptide comprises an acyl group modification at the N-terminus and an amide group modification at the carboxy terminus;
  (c) a peptide of from 10 to 30 amino acid residues, comprising the sequence DRVEPYSSTA (SEQ ID NO:14); and
  (d) a peptide of from 10 to 30 amino acid residues, comprising the sequence DRVEPYSSTA (SEQ ID NO:14), wherein said peptide:
    (i) comprises an acetyl modification at the N-terminus, and an amide group modification at the carboxy terminus (Peptide A, modified SEQ ID NO:14); or
    (ii) is in multimeric form linked via one or more lysine residues, and has the structure [{Ac-DRVEPYSSTA}2-K]2-K-OH (Peptide A(d), modified SEQ ID NO:14), wherein Ac is an acyl group.

* * * * *

SEQUENCE LISTING

```
<160> NUMBER OF SEQ ID NOS: 21

<210> SEQ ID NO 1
<211> LENGTH: 4
<212> TYPE: PRT
<213> ORGANISM: UNKNOWN
<220> FEATURE:
<223> OTHER INFORMATION: SYNTHETIC PEPTIDE
<220> FEATURE:
<221> NAME/KEY: MISC_FEATURE
<222> LOCATION: (1)..(1)
<223> OTHER INFORMATION: X = Glu or Asp
<220> FEATURE:
<221> NAME/KEY: MISC_FEATURE
<222> LOCATION: (2)..(3)
<223> OTHER INFORMATION: X = ANY AMINO ACID
<220> FEATURE:
<221> NAME/KEY: MISC_FEATURE
<222> LOCATION: (4)..(4)
<223> OTHER INFORMATION: X = Glu or Asp

<400> SEQUENCE: 1

Xaa Xaa Xaa Xaa
1

<210> SEQ ID NO 2
<211> LENGTH: 4
<212> TYPE: PRT
<213> ORGANISM: UNKNOWN
<220> FEATURE:
<223> OTHER INFORMATION: SYNTHETIC PEPTIDE
<220> FEATURE:
<221> NAME/KEY: MISC_FEATURE
<222> LOCATION: (2)..(3)
<223> OTHER INFORMATION: X = ANY AMINO ACID

<400> SEQUENCE: 2

Glu Xaa Xaa Glu
1

<210> SEQ ID NO 3
<211> LENGTH: 4
<212> TYPE: PRT
<213> ORGANISM: UNKNOWN
<220> FEATURE:
<223> OTHER INFORMATION: SYNTHETIC PEPTIDE
<220> FEATURE:
<221> NAME/KEY: MISC_FEATURE
<222> LOCATION: (2)..(3)
<223> OTHER INFORMATION: X = ANY AMINO ACID

<400> SEQUENCE: 3

Glu Xaa Xaa Asp
1

<210> SEQ ID NO 4
<211> LENGTH: 4
<212> TYPE: PRT
```

```
<213> ORGANISM: UNKNOWN
<220> FEATURE:
<223> OTHER INFORMATION: SYNTHETIC PEPTIDE
<220> FEATURE:
<221> NAME/KEY: MISC_FEATURE
<222> LOCATION: (2)..(3)
<223> OTHER INFORMATION: X = ANY AMINO ACID

<400> SEQUENCE: 4

Asp Xaa Xaa Glu
1

<210> SEQ ID NO 5
<211> LENGTH: 4
<212> TYPE: PRT
<213> ORGANISM: UNKNOWN
<220> FEATURE:
<223> OTHER INFORMATION: SYNTHETIC PEPTIDE
<220> FEATURE:
<221> NAME/KEY: MISC_FEATURE
<222> LOCATION: (2)..(3)
<223> OTHER INFORMATION: X = ANY AMINO ACID

<400> SEQUENCE: 5

Asp Xaa Xaa Asp
1

<210> SEQ ID NO 6
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 6

Asp Arg Val Glu
1

<210> SEQ ID NO 7
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 7

Glu Gly Met Arg
1

<210> SEQ ID NO 8
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 8

Glu Met Gly Glu
1

<210> SEQ ID NO 9
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 9
```

```
Asp Arg Ser Glu
1

<210> SEQ ID NO 10
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 10

Asp Ala Val Glu
1

<210> SEQ ID NO 11
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 11

Glu Val Arg Asp
1

<210> SEQ ID NO 12
<211> LENGTH: 4
<212> TYPE: PRT
<213> ORGANISM: UNKNOWN
<220> FEATURE:
<223> OTHER INFORMATION: SYNTHETIC PEPTIDE

<400> SEQUENCE: 12

Glu Gly Gly Glu
1

<210> SEQ ID NO 13
<211> LENGTH: 6
<212> TYPE: PRT
<213> ORGANISM: UNKNOWN
<220> FEATURE:
<223> OTHER INFORMATION: SYNTHETIC PEPTIDE

<400> SEQUENCE: 13

Pro Tyr Ser Ser Thr Ala
1               5

<210> SEQ ID NO 14
<211> LENGTH: 10
<212> TYPE: PRT
<213> ORGANISM: UNKNOWN
<220> FEATURE:
<223> OTHER INFORMATION: SYNTHETIC PEPTIDE

<400> SEQUENCE: 14

Asp Arg Val Glu Pro Tyr Ser Ser Thr Ala
1               5                   10

<210> SEQ ID NO 15
<211> LENGTH: 6
<212> TYPE: PRT
<213> ORGANISM: UNKNOWN
<220> FEATURE:
<223> OTHER INFORMATION: SYNTHETIC PEPTIDE

<400> SEQUENCE: 15

Glu Gly Met Glu Gly Met
```

-continued

```
<210> SEQ ID NO 16
<211> LENGTH: 10
<212> TYPE: PRT
<213> ORGANISM: UNKNOWN
<220> FEATURE:
<223> OTHER INFORMATION: SYNTHETIC PEPTIDE

<400> SEQUENCE: 16

Asp Arg Ser Glu Pro Tyr Ser Ser Thr Ala
1               5                   10

<210> SEQ ID NO 17
<211> LENGTH: 10
<212> TYPE: PRT
<213> ORGANISM: UNKNOWN
<220> FEATURE:
<223> OTHER INFORMATION: SYNTHETIC PEPTIDE

<400> SEQUENCE: 17

Asp Ala Val Glu Pro Tyr Ser Ser Thr Ala
1               5                   10

<210> SEQ ID NO 18
<211> LENGTH: 12
<212> TYPE: PRT
<213> ORGANISM: UNKNOWN
<220> FEATURE:
<223> OTHER INFORMATION: SYNTHETIC PEPTIDE

<400> SEQUENCE: 18

Cys Asp Arg Val Glu Pro Tyr Ser Ser Thr Ala Cys
1               5                   10

<210> SEQ ID NO 19
<211> LENGTH: 13
<212> TYPE: PRT
<213> ORGANISM: UNKNOWN
<220> FEATURE:
<223> OTHER INFORMATION: SYNTHETIC PEPTIDE

<400> SEQUENCE: 19

Ser Ile Asp Arg Val Glu Pro Tyr Ser Ser Thr Ala Gln
1               5                   10

<210> SEQ ID NO 20
<211> LENGTH: 10
<212> TYPE: PRT
<213> ORGANISM: UNKNOWN
<220> FEATURE:
<223> OTHER INFORMATION: SYNTHETIC PEPTIDE

<400> SEQUENCE: 20

Ala Thr Ser Ser Tyr Pro Glu Val Arg Asp
1               5                   10

<210> SEQ ID NO 21
<211> LENGTH: 848
<212> TYPE: PRT
<213> ORGANISM: Homo sapiens

<400> SEQUENCE: 21

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
```

```
                    20                  25                  30
Val Gly Glu Ser Lys Phe Phe Leu Cys Gln Val Ala Gly Asp Ala Lys
             35                  40                  45

Asp Lys Asp Ile Ser Trp Phe Ser Pro Asn Gly Glu Lys Leu Thr Pro
         50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                 85                  90                  95

Val Val Thr Gly Glu Asp Gly Ser Glu Ser Glu Ala Thr Val Asn Val
             100                 105                 110

Lys Ile Phe Gln Lys Leu Met Phe Lys Asn Ala Pro Thr Pro Gln Glu
         115                 120                 125

Phe Arg Glu Gly Glu Asp Ala Val Ile Val Cys Asp Val Val Ser Ser
     130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                 165                 170                 175

Arg Gly Ile Lys Lys Thr Asp Glu Gly Thr Tyr Arg Cys Glu Gly Arg
             180                 185                 190

Ile Leu Ala Arg Gly Glu Ile Asn Phe Lys Asp Ile Gln Val Ile Val
         195                 200                 205

Asn Val Pro Pro Thr Ile Gln Ala Arg Gln Asn Ile Val Asn Ala Thr
     210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                 245                 250                 255

Glu Glu Asp Asp Glu Lys Tyr Ile Phe Ser Asp Asp Ser Ser Gln Leu
             260                 265                 270

Thr Ile Lys Lys Val Asp Lys Asn Asp Glu Ala Glu Tyr Ile Cys Ile
         275                 280                 285

Ala Glu Asn Lys Ala Gly Glu Gln Asp Ala Thr Ile His Leu Lys Val
     290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                 325                 330                 335

Pro Ser Ile Thr Trp Arg Thr Ser Thr Arg Asn Ile Ser Ser Glu Glu
             340                 345                 350

Lys Thr Leu Asp Gly His Met Val Val Arg Ser His Ala Arg Val Ser
         355                 360                 365

Ser Leu Thr Leu Lys Ser Ile Gln Tyr Thr Asp Ala Gly Glu Tyr Ile
     370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                 405                 410                 415

Trp Glu Gly Asn Gln Val Asn Ile Thr Cys Glu Val Phe Ala Tyr Pro
             420                 425                 430

Ser Ala Thr Ile Ser Trp Phe Arg Asp Gly Gln Leu Leu Pro Ser Ser
         435                 440                 445
```

-continued

```
Asn Tyr Ser Asn Ile Lys Ile Tyr Asn Thr Pro Ser Ala Ser Tyr Leu
            450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                    485                 490                 495

Ala Asp Thr Pro Ser Ser Pro Ser Ile Asp Gln Val Glu Pro Tyr Ser
                500                 505                 510

Ser Thr Ala Gln Val Gln Phe Asp Glu Pro Glu Ala Thr Gly Gly Val
            515                 520                 525

Pro Ile Leu Lys Tyr Lys Ala Glu Trp Arg Ala Val Gly Glu Glu Val
            530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
                580                 585                 590

Phe Lys Thr Gln Pro Val Gln Gly Glu Pro Ser Ala Pro Lys Leu Glu
            595                 600                 605

Gly Gln Met Gly Glu Asp Gly Asn Ser Ile Lys Val Asn Leu Ile Lys
610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
                660                 665                 670

Tyr Val Val Ala Glu Asn Gln Gln Gly Lys Ser Lys Ala Ala His Phe
            675                 680                 685

Val Phe Arg Thr Ser Ala Gln Pro Thr Ala Ile Pro Ala Asn Gly Ser
            690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
                740                 745                 750

Ala Gly Pro Gly Ala Lys Gly Lys Asp Met Glu Glu Gly Lys Ala Ala
            755                 760                 765

Phe Ser Lys Asp Glu Ser Lys Glu Pro Ile Val Glu Val Arg Thr Glu
770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
                820                 825                 830

Thr Val Pro Asn Asp Ala Thr Gln Thr Lys Glu Asn Glu Ser Lys Ala
            835                 840                 845
```